(12) United States Patent
Hampton et al.

(10) Patent No.: US 10,563,174 B2
(45) Date of Patent: Feb. 18, 2020

(54) PROTEINS INCREASING PANCREATIC BETA CELL NUMBER AND METHODS OF USE

(71) Applicant: University of Oregon, Eugene, OR (US)

(72) Inventors: Jennifer Hampton, Eugene, OR (US); Karen Guillemin, Eugene, OR (US)

(73) Assignee: University of Oregon, Eugene, OR (US)

( * ) Notice: Subject to any disclaimer, the term of this patent is extended or adjusted under 35 U.S.C. 154(b) by 236 days.

(21) Appl. No.: 15/513,117

(22) PCT Filed: Sep. 23, 2015

(86) PCT No.: PCT/US2015/051744
§ 371 (c)(1),
(2) Date: Mar. 21, 2017

(87) PCT Pub. No.: WO2016/049200
PCT Pub. Date: Mar. 31, 2016

(65) Prior Publication Data
US 2017/0292115 A1    Oct. 12, 2017

Related U.S. Application Data

(60) Provisional application No. 62/167,061, filed on May 27, 2015, provisional application No. 62/054,685, filed on Sep. 24, 2014.

(51) Int. Cl.
| | |
|---|---|
| *A61K 39/00* | (2006.01) |
| *C12N 5/071* | (2010.01) |
| *A61K 35/39* | (2015.01) |
| *A61K 38/02* | (2006.01) |
| *C07K 14/47* | (2006.01) |

(52) U.S. Cl.
CPC ........... *C12N 5/0676* (2013.01); *A61K 35/39* (2013.01); *A61K 38/02* (2013.01); *C07K 14/474* (2013.01); *C07K 2319/00* (2013.01); *C12N 2506/22* (2013.01)

(58) Field of Classification Search
CPC .................................................. C12N 5/0676
See application file for complete search history.

(56) References Cited

U.S. PATENT DOCUMENTS 5,846,936 A * 12/1998 Felix ...................... C07K 14/60
514/11.2
2003/0180813 A1 * 9/2003 Ohishi ................ C07K 14/705
435/7.2

OTHER PUBLICATIONS

Tsuji et al., "Whole Organism High Content Screening Identifies Stimulators of Pancreatic Beta-Cell Proliferation," *PLOS One*, 9(8):e104112, 2014 (9 pages).
Brennand et al., "Slow and steady is the key to β-cell replication," *Journal of Cellular and Molecular Medicine*, vol. 13, No. 3, pp. 472-487, 2009.
Database ENA, Accession No. AEB49130, Apr. 14, 2011 (1 page).
Database UniProt, Accession No. K1JN70, Nov. 28, 2012 (1 page).
Database UniProt, Accession No. V9ZZ31, Mar. 19, 2014 (1 page).
Elo et al, "Larval zebrafish as a model for glucose metabolism: expression of phosphoenolpyruvate carboxykinase as a marker for exposure to anti-diabetic compounds," *Journal of Molecular Endocrinology*, vol. 38, Nos. 3-4, pp. 433-440, 2007.
Hampton et al., "Microbial signaling mechanisms important for pancreatic β cell development in zebrafish," *Microbial Ecology and Theory of Animals Symposium*, Aug. 8-10, 2014 (1 page).
Silver et al., "Identification of *Aeromonas veronii* genes required for colonization of the medicinal leech, *Hirudo verbana*," *Journal of Bacteriology*, vol. 189, No. 19, pp. 6763-6772, 2007.
Walpita et al., "A Human Islet Cell Culture System for High-Throughput Screening," *Journal of Biomolecular Screening*, vol. 17, No. 4, pp. 509-518, 2012.

* cited by examiner

*Primary Examiner* — Albert M Navarro
(74) *Attorney, Agent, or Firm* — Klarquist Sparkman, LLP

(57) ABSTRACT

Disclosed herein are bacterial proteins that increase pancreatic beta (β) cell number and/or proliferation, methods of increasing β cell number and/or proliferation using such proteins, and methods of treating or inhibiting diabetes in a subject by administering such proteins to the subject. In some embodiments, the protein has at least 80% sequence identity to the amino acid sequence set forth as any one of SEQ ID NOs: 1-7, or fragments thereof. Recombinant vectors including a nucleic acid encoding the protein (such as a nucleic acid encoding a protein with at least 80% sequence identity to any one of SEQ ID NOs: 1-7 or fragments thereof) operably linked to a heterologous promoter are also disclosed. Also disclosed are methods of identifying compounds that increase β cell number and/or proliferation by determining the effect of test compounds on β cell number or proliferation in zebrafish pancreas.

16 Claims, 12 Drawing Sheets

Specification includes a Sequence Listing.

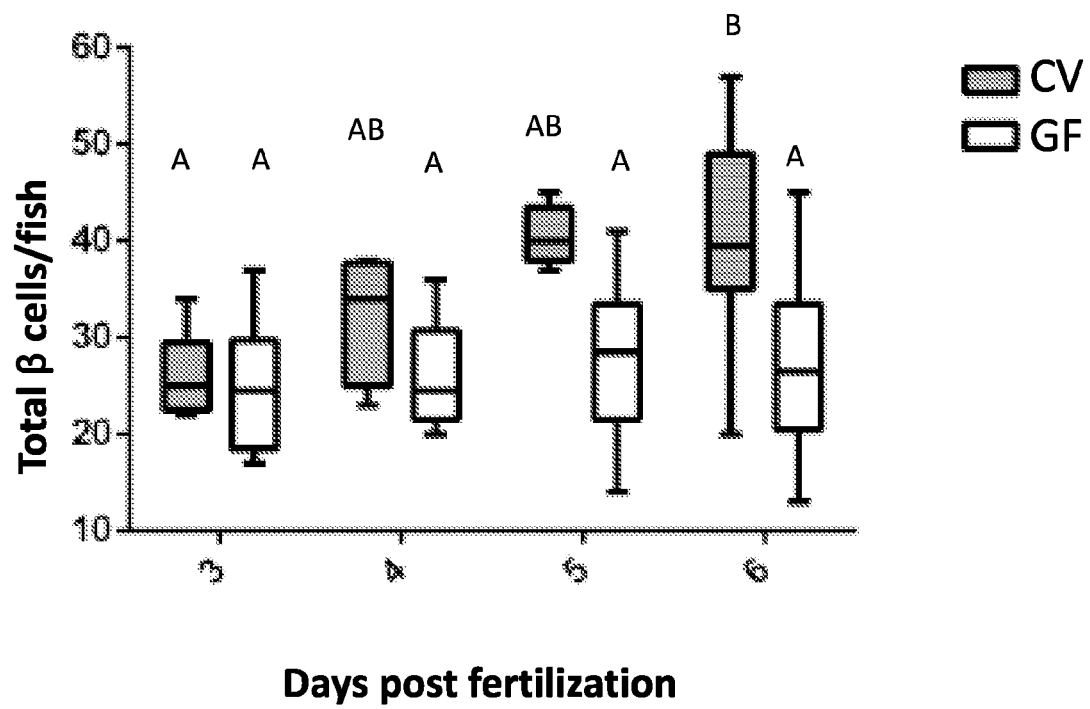
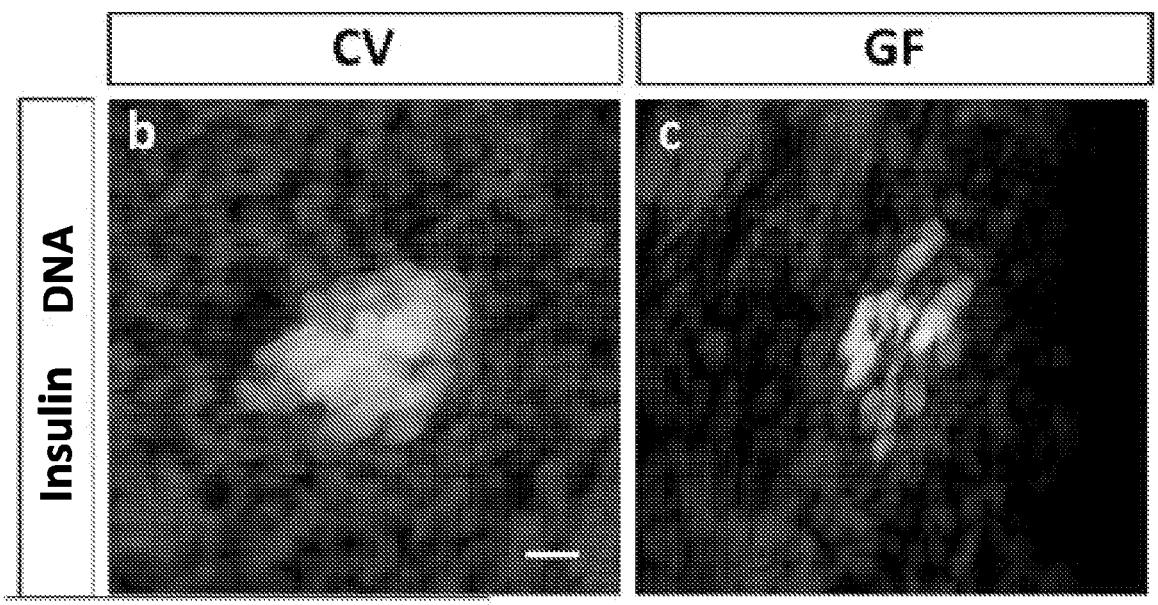
FIG. 1A
FIG. 1B  FIG. 1C

PROTEINS INCREASING PANCREATIC BETA CELL NUMBER AND METHODS OF USE

CROSS REFERENCE TO RELATED APPLICATIONS

This is the § 371 U.S. National Stage of International Application No. PCT/US2015/051744, filed Sep. 23, 2015, which was published in English under PCT Article 21(2), which in turn claims the benefit of U.S. Provisional Application No. 62/054,685, filed Sep. 24, 2014, and U.S. Provisional Application No. 62/167,061, filed May 27, 2015, both of which are incorporated herein by reference in their entirety.

ACKNOWLEDGMENT OF GOVERNMENT SUPPORT

This invention was made with government support under grant numbers P50 GM098911-03A1 and T32 GM007413-37 awarded by the National Institutes of Health. The government has certain rights in the invention.

FIELD

This disclosure relates to proteins from gut microbiota, particularly proteins that increase β-cells in the pancreas, methods of their use, and methods for identifying such proteins.

BACKGROUND

Diabetes is an increasingly common disease, with about 8-9% of the U.S. population diagnosed with diabetes and over 35% of the U.S. population having prediabetes. Individuals with diabetes are at increased risk for heart disease, stroke, blindness, kidney failure, and peripheral neuropathy (and potential loss of lower limbs). The development of both Type I and Type II diabetes is likely to involve a combination of genetic and environmental factors. Type I diabetes results from destruction of insulin-producing β cells in the pancreas. Treatment includes administration of insulin by injection or pump. Type II diabetes includes insulin resistance, which gradually leads to a decrease or loss of insulin production by β cells in the pancreas.

SUMMARY

Despite the development of treatments for diabetes, there remains a need for additional diabetes therapies, particularly for Type I diabetes. The inventors have surprisingly identified a protein from the gut bacterium *Aeromonas* that increases the number of pancreatic β cells (for example, increases proliferation, differentiation, and/or survival of pancreatic β cells), and which could be used to treat or inhibit diabetes in a subject.

Disclosed herein are polypeptides that increase pancreatic β cell number. In some embodiments, the polypeptides have at least 80% sequence identity to any one of SEQ ID NOs: 1-7 disclosed herein or a fragment thereof (such as a SYLF domain, for example, a fragment corresponding to amino acids 114-258 of any of SEQ ID NOs: 1-3). Also disclosed are polynucleotides that encode the polypeptides, including nucleic acids with at least 80% sequence identity to any one of SEQ ID NOs: 8-11 or a fragment thereof (for example, a nucleic acid encoding a SYLF domain, such as a nucleic acid corresponding to nucleotides 340-774 of any one of SEQ ID NOs: 8-10).

Recombinant vectors including a nucleic acid encoding the herein identified proteins that increases pancreatic β cell number (such as a nucleic acid encoding a protein with at least 80% sequence identity to any one of SEQ ID NOs: 1-7 or a fragment thereof) operably linked to a heterologous promoter are also disclosed. In some examples, the nucleic acid encoding the protein is set forth in SEQ ID NOs: 8-11. Cells including the recombinant vector (for example, cells transformed with the vector) are also disclosed.

Disclosed herein are methods of treating or inhibiting diabetes (such as type I diabetes) in a subject by administering to a subject a protein disclosed herein, a nucleic acid encoding the protein, a cell expressing the protein, or a composition including the protein. In some embodiments, the protein has at least 80% sequence identity to the amino acid sequence set forth as any one of SEQ ID NOs: 1-7 or fragments thereof. Also disclosed are methods of increasing β cell number or proliferation, by contacting pancreatic cells with a protein disclosed herein, a nucleic acid encoding the protein, a cell expressing the protein, or a composition including the protein.

Also disclosed herein are methods of identifying compounds that increase β cell number by determining the effect of test compounds on β cell number or proliferation in zebrafish pancreas. In some embodiments, germ-free zebrafish are contacted with one or more test compounds (such as a defined bacterial strain, an extract from a defined bacterial strain, or one or more compounds) and the number of β cells in the pancreas of the zebrafish are measured and compared to a control. In one specific example, the zebrafish is a transgenic zebrafish expressing green fluorescent protein (GFP) or another marker under the control of the insulin promoter. This system permits measurement of β cell number in the pancreas of living organisms.

The foregoing and other features of the disclosure will become more apparent from the following detailed description, which proceeds with reference to the accompanying figures.

BRIEF DESCRIPTION OF THE DRAWINGS

FIGS. 1A-E are a series of panels showing that bacteria are required for normal expansion of the β cell mass. FIG. 1A is a graph showing the total number of beta cells per larvae in GF (white box plots) and CV (grey box plots) zebrafish at 3, 4, 5 and 6 days post-fertilization (dpf). Single factor ANOVA indicates that gnotobiology of the fish was significant in determining the number of β cells present ($F_7$=9.01, p=1.45e$^{-8}$). Labels A, AB and B indicate results of post hoc means testing (Tukey). The difference between GF and CV cell counts became significant at 6 dpf (t=-5.91, p<0.001). This significance is consistent across FIGS. 1B-E. Z-projections of confocal scans through the primary islet are shown for CV (FIG. 1B) and GF (FIG. 1C) Tg(-1.0insulin:eGFP) larvae age 6 dpf. Cells were stained for insulin (β cells) and nuclei. Scale bar=10 μm. FIG. 1D is a graph showing quantification of β cells in GF larvae treated at 4 dpf with either non-sterile tank water (XGF) or mono-associated with the indicated bacterial strain isolated from the zebrafish gut. Bacterial mono-associations are labeled by genus. *Aeromonas* sp. are also labeled with a strain identifier (HM21, ZF1 & ZF2). All fish in this, and subsequent figures, were quantified at 6 dpf. Data represented in shaded box plots, here and in all subsequent figures, were found to be significantly greater (p<0.05) than GF controls via Tukey analysis. FIG. 1E is a graph showing average amount of glucose (pmol) per larvae aged 6 dpf*$t_{17}$=−3.65, p<0.01.

In all relevant panels and remaining figures, box plot whiskers represent the minimum and maximum values of the data set. *Vibrio* (*) colonized the zebrafish gut, but did not induce β cell expansion FIG. 2A is a graph showing that bacterial isolates of the zebrafish gut are capable of forming mono-associations with larvae. The graph shows quantification of the CFU per gut in each strain that was assayed in FIG. 1D. Shaded box plots denote strains which were sufficient to rescue GF β cell numbers (as shown in FIG. 1D), dashed line denotes limit of detection. FIG. 2B is a graph showing CFU detected from zebrafish with di-association of *A. veronii* WT and *A. veronii* ΔbefA strains. When inoculated in a 1:1 ratio, the WT strain colonized the gut at slightly higher (though not statistically significant) levels that the ΔbefA strain. *Vibrio* (*) colonized the zebrafish gut, but did not induce β cell expansion FIG. 3A is a graph showing total β cell numbers in GF fish treated at 4 dpf with different samples of cell free supernatant (CFS). WT represents wild type *A. veronii*. +PK indicates proteinase K was added to the CFS sample prior to treatment. ΔT2SS represents the *A. veronii*$^{\Delta T2SS}$ mutant. FIG. 3B is a graph showing total β cells in GF fish treated with various mono-associations (MA) or samples of CFS. 10165 represents purified protein from the M001_10165 locus (also referred to as BefA). ΔbefA represents the *A. veronii*$^{\Delta befA}$ mutant strain. FIGS. 3C-3E are a series of digital images of Z-projections of confocal scans through the primary islet of GF (FIG. 3C), CV (FIG. 3D), and 10165 protein treated (FIG. 3E) Tg(−1.0insulin:eGFP) larvae age 6 dpf stained for insulin and nuclei. Scale bar=10 μm.

FIG. 4A is a graph showing total β cell numbers in GF fish treated at 4 dpf with separate ammonium sulfate fractions prepared from the *A. veronii*$^{\Delta T2SS}$ CFS. FIG. 4B is a digital image of an SDS-page gel showing subsequent steps in the purification of BefA (predicted size of 29 kDa, arrow) from *E. coli* cell lysate, lane 1: ladder, lane 2: cell lysate after IPTG induction, lane 3: supernatant from cell lysate after the addition of nickel beads, lane 4: 20 mM imidazole wash step, lanes 5-8: elutions of BefA from nickel beads.

FIGS. 5A-5F are images of representative 2D slices from confocal scans through the primary islets of CV (FIGS. 5A-5B), GF (FIGS. 5C-5D), and BefA-treated (FIGS. 5E-5F) Tg(−1.0insulin:eGFP) larvae age 6 dpf showing relative levels of proliferating cells marked with EdU, insulin, and nuclei. Scale bar=10 μm. The perimeter of insulin expression is marked with a dotted white line (FIGS. 5B, 5D, and 5F). FIG. 5G is a graph showing quantification of the percentage of EdU labeled β cells per fish. FIG. 5H is a graph showing quantification of the percentage of EdU labeled cells from murine β-TC-6 cultures following treatment with BefA or a control. ***$t_{43.99}$=4.28, p<0.0001. FIG. 5I is representative merged image of β-TC-6 cells stained with nuclei, insulin, and EdU.

FIG. 6A is a graph showing quantification of EdU$^+$ pancreatic exocrine cells in CV, GF or BefA treated GF fish. FIG. 6B is a graph showing quantification of EdU$^+$ intestinal epithelial cells in CV, GF or BefA treated GF fish. FIG. 6C is a representative image of IEC-6 cells showing nuclei and EdU.

FIG. 7A shows close homologs of BefA across microbial species. Each species is represented by its closest BefA homolog, with a minimum allowed amino acid sequence identity of 50% (relative to the query sequence). Notably, the *Enterococcus gallinarum* homolog clusters among homologs from the *Aeromonas* genus, which is evidence of a possible lateral gene transfer event. FIG. 7B shows BefA phylogeny including more distant homologs (sequence identity >20%) and grouped by genus. The portion of the tree represented in FIG. 7A is contained in the light gray box. *Enterococcus, Enterobacter, Klebsiella*, and *Escherichia* are genera that were associated with humans in metagenomes produced during the Human Microbiome Project. In both FIGS. 7A and 7B, the numbers indicate branch support (values closer to 1 are better supported); branches with support values <0.5 have been collapsed. Scale bars indicate amino acid substitutions per amino acid site.

SEQUENCE LISTING

Figure 1D:
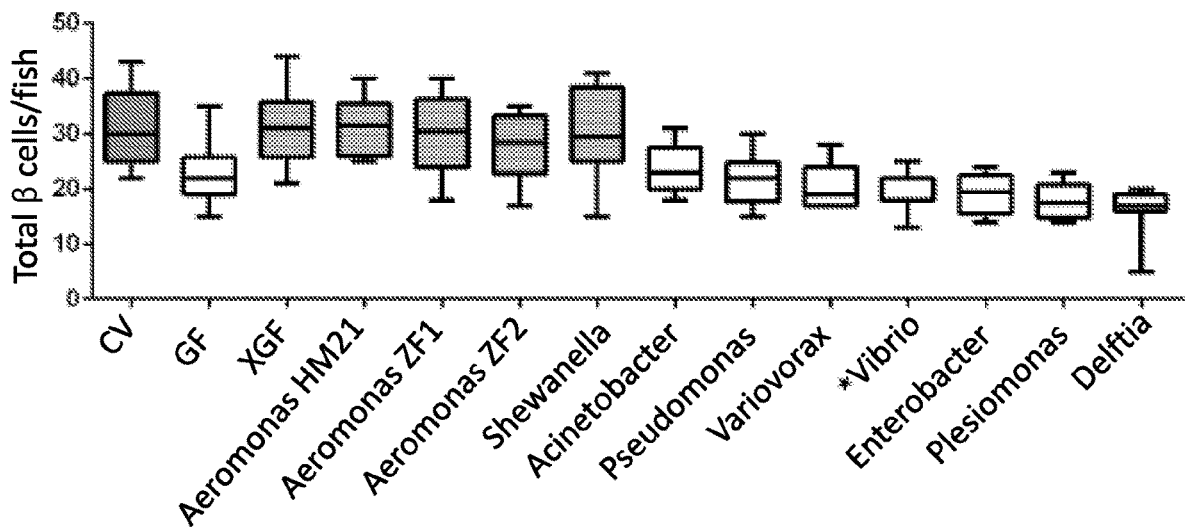

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Mar. 16, 2017, and is 19,892 bytes, which is incorporated by reference herein.

SEQ ID NOs: 1-3 are exemplary amino acid sequences of an *Aeromonas* protein that increases pancreatic β cell number.

SEQ ID NO: 4 is an exemplary amino acid sequence of a putative *Shewanella* protein that increases β cell number.

SEQ ID NO: 5 is an exemplary amino acid sequence of a putative *Klebsiella* protein that increases β cell number.

SEQ ID NO: 6 is an exemplary amino acid sequence of a putative *Enterococcus gallinarum* protein that increases β cell number.

SEQ ID NO: 7 is an exemplary amino acid sequence of a putative *Photobacterium* protein that increases β cell number.

SEQ ID NOs: 8-10 is are nucleic acid sequence encoding the amino acid sequence of SEQ ID NOs: 1-3, respectively.

SEQ ID NO: 11 is a nucleic acid sequence encoding the amino acid sequence of SEQ ID NO: 4.

SEQ ID NOs: 12 and 13 are primers for the amplification of the *Aeromonas* nucleic acid of SEQ ID NO: 8.

DETAILED DESCRIPTION

Type I diabetes is a prevalent and costly disease characterized by the loss of insulin secreting β cells of the endocrine pancreas (Van Belle et al., *Physiol. Rev.* 91:79-118, 2011). Successful treatments for the disease, beyond exogenous insulin injections, remain elusive despite the fact that the number of diagnosed cases has been increasing steadily over the past several decades (Patterson et al., *Lancet* 373:2027-2033, 2009). Modern lifestyle changes, such as antibiotic use and an ever-increasing emphasis on cleanliness, have been theorized to reduce environmental exposure to unique bacterial symbionts that could be essential to health and development (Blaser and Falkow, *Nat. Rev. Micro.* 7:887-894, 2009). Interestingly, the gastrointestinal-associated microbiota is emerging as a potential major environmental factor in the onset of type I diabetes, though the mechanisms through which bacteria influence disease etiology are unknown (Fung et al., *Curr. Allergy/Asthma Rep.* 12:511-519, 2012).

The microbiota has been shown to play a role in many different aspects of animal development (Fraune and Bosch, *Bioessays* 32:571-580, 2010). The pancreas and the intestine are intricately connected, both during development and throughout adulthood (Field et al., *Dev. Biol.* 261:197-208, 2003). Furthermore, communication between these two organs is essential in order to regulate metabolic homeostasis. Therefore, it is believed that signals from the intestinal microbiota influence β cell development and/or function. Using the larval zebrafish as a model for pancreas development, and gnotobiotic methods, the inventors show herein that the loss of host-associated bacteria results in a decrease in the total number of β cells in the developing pancreas. Furthermore, exposure to individual bacterial species results in the restoration of β cell numbers to conventionally reared control levels, and that a secreted bacterial protein is responsible for this effect. The protein is believed to increase the number of β cells in the pancreas by stimulating β cell proliferation, increasing β cell production or differentiation, increasing β cell survival, or a combination thereof.

As described herein, it has surprisingly been found that *A. veronii* and other bacterial strains in possession of the befA locus exert their influence on the pancreas from their location within the gut, since a secreted product from the gut-associated microbiota has herein been shown to affect critical developmental processes in a separate organ. It is important to note that the pancreas and the gut, despite being physically separated, rely on vital connections to coordinate the physiological functions of digestion and metabolic homeostasis. If these bacterial signals require direct interaction with β cells, they could reach the pancreas by utilizing these inter-organ connections. For instance, the pancreas secretes digestive enzymes into the gut lumen through the extra pancreatic duct (Field et al., *Dev. Biol.* 261:197-208, 2003). This duct offers a direct pathway between the pancreas and the microbiota within the gut lumen. Furthermore, bacteria and bacterial products can enter the portal vein, which supplies both the liver and the pancreas with blood after it leaves the intestine (Minemura et al., *World J. Gastroenterol.* 21:1691-172, 2015). Alternatively, the bacterial signal could act on β cells in an indirect manner, by binding an intermediate host cell type, such as enteroendocrine cells of the intestine (Cani et al., *Curr. Opin. Pharmacol.* 13:935-940, 2013).

Several studies have shown that fecal bacterial communities of diabetic children are less diverse than those of healthy (non-diabetic) children (Giongo et al., *ISME J.* 5:82-91, 2011; Kostic et al., *Cell Host Microbe* 17:260-273, 2015; Murri et al., *BMC Med.* 11:46, 2013; Mejia-Leon et al., *Sci. Rep.* 4:3814, 2014). Even more striking, there is evidence that this shift in the bacterial community occurs prior to disease onset (Kostic et al., *Cell Host Microbe* 17:260-273, 2015). It is shown herein that an important host developmental process involves the presence of a protein produced only in a subset of bacterial species. It is possible that the failure to maintain microbial diversity, as has been shown in patients with type I diabetes, could result in the loss of important bacterial signals required for robust β cell development early in life.

I. Abbreviations

BefA β cell expansion factor A
CFS cell-free supernatant
CFU colony-forming units
CV conventionally reared
dpf days post-fertilization
EdU 5-ethynyl-2'-deoxyuridine
EM embryo medium
EPD extra-pancreatic duct
GF germ-free reared
GFP green fluorescent protein
T2SS type 2 secretion system II. Terms Unless otherwise noted, technical terms are used according to conventional usage. Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Although methods and materials similar or equivalent to those described herein can be used in the practice or testing of the present disclosure, suitable methods and materials are described below.

All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Beta (β) cells: A type of cell in the pancreas that secretes insulin. These cells also secrete C-peptide and amylin in addition to insulin. The β cells are present in the islets of Langerhans in the pancreas and make up about 65-80% of the islets.

Diabetes mellitus: A disease caused by a relative or absolute lack of insulin leading to uncontrolled carbohydrate metabolism, commonly simplified to "diabetes." As used herein, "diabetes" refers to diabetes mellitus, unless otherwise indicated. A "diabetic condition" includes pre-diabetes and diabetes. Type 1 diabetes (sometimes referred to as "insulin-dependent diabetes" or "juvenile-onset diabetes") is an auto-immune disease characterized by destruction of the pancreatic β cells that leads to a total or near total lack of insulin. In type 2 diabetes (sometimes referred to as "non-insulin-dependent diabetes" or "adult-onset diabetes"), the body does not respond to insulin, though it is present.

Symptoms of diabetes include: excessive thirst (polydipsia); frequent urination (polyuria); extreme hunger or constant eating (polyphagia); unexplained weight loss; presence of glucose in the urine (glycosuria); tiredness or fatigue; changes in vision; numbness or tingling in the extremities (hands, feet); slow-healing wounds or sores; and abnormally high frequency of infection. Diabetes may be clinically diagnosed by a fasting plasma glucose concentration of greater than or equal to 7.0 mmol/L (126 mg/dL), or a plasma glucose concentration of greater than or equal to 11.1 mmol/L (200 mg/dL) at about two hours after an oral glucose tolerance test with a 75 g load. A more detailed description of diabetes may be found in *Cecil Textbook of Medicine*, Goldman, et al., eds. (Elsevier, 2003, $22^{nd}$ ed.).

Effective amount: An amount of an agent or composition that alone, or together with a pharmaceutically acceptable carrier and/or one or more additional agents, induces the desired response. In some embodiments, an effective amount is an amount that increases pancreatic β cell number of proliferation or an amount that delays, reduces, or ameliorates or one more symptoms of diabetes in a subject. Effective amounts of an agent can be determined in many different ways, such as assaying for cell number (such asp cell number or proliferation, for example at least a 10%, 20%, 30%, 40%, 50%, 60%, 70%, 80%, 90%, 100%, or more increase in (cell number or proliferation), delay (or even prevention) of onset of a condition associated with β cells (such as diabetes), or a reduction or amelioration of one or more symptoms of a subject with diabetes (such as at least a 10%, 20%, 30%, 40%, 50%, 60%, 70%, 80%, 90%, 95%, or more reduction in one or more symptoms of diabetes). Effective amounts also can be determined through various in vitro, in vivo or in situ assays, including, but not limited to those described herein.

Germ-free: An animal born and reared in aseptic conditions having substantially no microorganisms living on or in it (for example, substantially no bacteria in the gut of the animal).

Gnotobiotic: An animal in which only known strains of microorganisms are present. For example, a germ-free animal exposed to (e.g., intentionally inoculated with) one or more known bacterial strains is gnotobiotic. Germ-free animals are also gnotobiotic, as their microbial status is known. In contrast, conventionally reared animals (born and raised without absolute control of microorganism exposure) have a microbiota of many, and in most cases hundreds or thousands of organisms, which population will vary from animal to animal.

Heterologous: Originating from a different genetic sources or species. For example, a nucleic acid that is heterologous to a cell originates from an organism or species other than the cell in which it is expressed. In one specific, non-limiting example, a heterologous nucleic acid includes an *Aeromonas* nucleic acid that is present or expressed in a different bacterial cell (such as an *E. coli* cell) or in an algal, plant, or mammalian cell. Methods for introducing a heterologous nucleic acid into bacterial, algal, plant, and mammalian cells are well known in the art, for example transformation with a nucleic acid, including electroporation, lipofection, and particle gun acceleration.

In another example of use of the term heterologous, a nucleic acid operably linked to a heterologous promoter is from an organism or species other than that of the promoter. For example, an *Aeromonas* nucleic acid may be linked to a heterologous bacterial, viral, or mammalian promoter. In other examples of the use of the term heterologous, a nucleic acid encoding a polypeptide (such as a protein increasing β cell number disclosed herein) or portion thereof is operably linked to a heterologous nucleic acid encoding a second polypeptide or portion thereof, for example to form a non-naturally occurring fusion protein.

Isolated: An "isolated" biological component (such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and/or cells. Nucleic acid molecules and proteins that have been "isolated" include nucleic acid molecules and proteins purified by standard purification methods or prepared by recombinant expression in a host cell, as well as chemically synthesized nucleic acid molecules and proteins.

Operably linked: A first nucleic acid is operably linked with a second nucleic acid when the first nucleic acid is placed in a functional relationship with the second nucleic acid. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carrier: The pharmaceutically acceptable carriers useful in this disclosure are conventional. *Remington: The Science and Practice of Pharmacy*, The University of the Sciences in Philadelphia, Editor, Lippincott, Williams, & Wilkins, Philadelphia, Pa., $21^{st}$ Edition (2005), describes compositions and formulations suitable for pharmaceutical delivery of one or more therapeutic agents, such as those disclosed herein.

In general, the nature of the carrier will depend on the particular mode of administration employed. For instance, parenteral formulations usually comprise injectable fluids that include pharmaceutically and physiologically acceptable fluids such as water, physiological saline, balanced salt solutions, aqueous dextrose, glycerol, or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, pH buffering agents, or the like, for example sodium acetate or sorbitan monolaurate.

Proliferation: An increase in cell number, for example by cell division.

Recombinant: A nucleic acid or protein that is not naturally occurring or has a sequence that is made by an artificial combination of two otherwise separated segments of nucleotides or amino acids. This artificial combination is often accomplished by chemical synthesis or, more commonly, by the artificial manipulation of isolated segments of nucleic acids, e.g., by genetic engineering techniques such as those described in Sambrook et al. *Molecular Cloning: A Laboratory Manual*, $3^{rd}$ ed., Cold Spring Harbor Laboratory Press, NY, 2001. The term recombinant includes nucleic acids or proteins that have been altered solely by addition, substitution, or deletion of a portion of the nucleic acid sequence or amino acid sequence, respectively.

Sample (or biological sample): A specimen containing genomic DNA, RNA (including mRNA), protein, or combinations thereof, obtained from a subject. Examples include, but are not limited to, peripheral blood (or fractions thereof), fine needle aspirate, urine, saliva, feces, tissue biopsy, surgical specimen, and autopsy material.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl.*

*Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations. The NCBI Basic Local Alignment Search Tool (BLAST) (Altschul et al., *J. Mol. Biol.* 215:403-10, 1990) is available from several sources, including the National Center for Biotechnology (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

One of skill in the art will appreciate that the particular sequence identity ranges provided herein are for guidance only; it is possible that strongly significant homologs or orthologs could be obtained that fall outside the ranges provided.

Subject: Living multi-cellular vertebrate organism, a category that includes vertebrates, including human and non-human mammals. In some examples, a subject includes laboratory animals, including mice or zebrafish.

SYLF domain: Also referred to as DUF500. A highly conserved lipid-binding (for example, phosphoinositide-binding) module present in proteins from bacteria to mammals. See, e.g., NCBI Conserved Domains Database Accession No. cd11524, incorporated herein by reference as present in the database on May 27, 2015.

Transduced and Transformed: A virus or vector "transduces" a cell when it transfers nucleic acid into the cell. A cell is "transformed" by a nucleic acid transduced into the cell when the DNA becomes replicated by the cell, either by incorporation of the nucleic acid into the cellular genome, or by episomal replication. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Treating or Inhibiting: "Inhibiting" refers to inhibiting or reducing the full development of a condition or disorder (such as diabetes) or one or more symptoms thereof. Inhibition of a condition or disorder can span the spectrum from partial inhibition (reduction) to substantially complete inhibition (prevention) of the condition or disorder or one or more symptoms thereof. In some examples, the term "inhibiting" refers to reducing or delaying the onset or progression of diabetes. In contrast, "treatment" refers to a therapeutic intervention that ameliorates a sign or symptom of a disease or pathological condition (such as diabetes) after it has begun to develop.

Vector: A nucleic acid molecule that can be introduced into a host cell, thereby producing a transformed or transduced host cell. Recombinant DNA vectors are vectors including recombinant DNA. A vector can include nucleic acid sequences that permit it to replicate in a host cell, such as an origin of replication. A vector can also include one or more selectable marker genes, a cloning site for introduction of heterologous nucleic acids, a promoter (for example for expression of an operably linked nucleic acid), and/or other genetic elements known in the art. Vectors include plasmid vectors, including plasmids for expression in gram negative and gram positive bacterial cell. Exemplary vectors include those for use in *E. coli*. Vectors also include viral vectors, such as, but not limited to, retrovirus, orthopox, avipox, fowlpox, capripox, suipox, adenovirus, herpes virus, alpha virus, baculovirus, Sindbis virus, vaccinia virus, and poliovirus vectors. Vectors also include vectors for expression in yeast cells or mammalian cells.

In some examples, a heterologous nucleic acid (such as a nucleic acid encoding an *Aeromonas* protein) is introduced into a vector to produce a recombinant vector, thereby allowing the nucleic acid to be renewably produced and or a protein encoded by the nucleic acid to be expressed.

III. Proteins Increasing β Cell Number

Disclosed herein are proteins from members of the intestinal microbiota, including *Aeromonas, Shewanella, Klebsiella, Enterococcus, Photobacterium,* and/or other bacteria that increase the number of β cells in the pancreas of a subject to which the protein is provided. In particular examples, the proteins increase β cell proliferation. In other examples, the proteins increase β cell number by mechanisms other than, or in addition to, increasing β cell proliferation.

In some embodiments the protein is a polypeptide which includes, consists essentially of, or consists of the amino acid sequence set forth as any one of SEQ ID NOs: 1-3. In additional embodiments, a polypeptide increasing β cell number disclosed herein has at least 50%, 55%, 60%, 65%, 70%, 75%, 80%, 85%, 90%, 95%, 96%, 97%, 98%, or 99% sequence identity to the amino acid sequence set forth in SEQ ID NOs: 1-3, for example from *Aeromonas* (such as *A. veronii*) or *Shewanella* (such as *S. oneidensis*). In some examples herein, the protein is referred to as BefA (and the corresponding nucleic acid is referred to as befA). Exemplary sequences can be obtained using computer programs that are readily available on the internet and the amino acid sequences set forth herein. In some examples, the polypeptide retains a function of the disclosed protein, such as increasing the number of β cells and/or reducing or inhibiting one or more signs or symptoms of diabetes (such as type I diabetes) in a subject.

In additional embodiments, a protein increasing β cell numbers (such as SEQ ID NOs: 1-3) includes a portion or fragment of the protein (for example, a portion of an *Aeromonas* protein disclosed herein). In some examples, the protein or portion or fragment thereof includes at least 20 contiguous amino acids of a disclosed protein, for example, at least 30, at least 50, at least 75, at least 100, at least 150, at least 200, at least 250, or more amino acids of a protein increasing β cell number, such as SEQ ID NOs: 1-3. In other examples, the protein or portion thereof includes at least the first half, the second half, at least one third, at least one quarter, at least one fifth of the protein, or any combination thereof (such as at least two thirds, at least two quarters, at least three fifths, and so on). In other examples, a portion or fragment of a protein increasing β cell number includes one or more domains of the protein. In some examples, a domain may include a SYLF domain, such as amino acids 114-258 of any one of SEQ ID NOs: 1-3. In some examples, the protein or a fragment thereof includes, consists essentially of, or consists of a SYLF domain. In other examples, the protein or fragment thereof is a processed or mature protein, for example, a protein lacking the putative secretion signal sequence corresponding to amino acids 1-21 of SEQ ID NO: 1). One of ordinary skill in the art will recognize that the boundaries of a domain (such as a SYLF domain or a secretion signal sequence) is not exact, and in some examples may include additional or fewer amino acids (for example, about 20, 19, 18, 17, 16, 15, 14, 13, 12, 11, 10, 9, 8, 7, 6, 5, 4, 3, 2, or 1 more or less amino acids from either end of the domain). In some examples, the fragment of the polypeptide retains a function of the disclosed proteins, such as increasing the number of β cells and/or reducing or inhibiting one or more signs or symptoms of diabetes (such as type I diabetes) in a subject. One of ordinary skill in the art can identify the corresponding domains from other proteins that increase β cell numbers, for example a protein from another bacterium or other organism.

Exemplary *Aeromonas* proteins that increase β cell number include the amino acid sequences of GenBank Accession Nos. ERF65753 (SEQ ID NO: 1), YP_004391747, WP_019445797, WP_005334756, WP_005362069, WP_005347598, WP_026456068, WP_019839625, and WP_005298756; all of which are incorporated herein by reference as present in GenBank on Sep. 22, 2014.

Additional proteins increasing β cell number include proteins with at least 50% (such as at least 55%, 60%, 65%, 70%, 75%, or more identity) sequence identity to SEQ ID NOs: 1-3 or at least 20% (such as at least 30%, 40%, 50%, 60%, 70%, 80%, or more identity) to a fragment of SEQ ID NOs: 1-3, such as the SYLF domain (corresponding to amino acids 114-258 of SEQ ID NOs: 1-3). Exemplary proteins include a protein including, consisting essentially of, or consisting of SEQ ID NOs: 4-7. Other examples include *Photobacterium* proteins having the amino acid sequences of GenBank Accession Nos. WP_007468440 (SEQ ID NO: 7) and GAL02513 and *Vibrio* proteins having the amino acid sequences of GenBank Accession Nos. WP_025555898 and KED81752, all of which are incorporated herein by reference as present in GenBank on Sep. 22, 2014. One of ordinary skill in the art can identify additional proteins increasing β cell number, for example from other microbiota, for example utilizing the methods described below.

Minor modifications of an *Aeromonas* (or another microbial) protein increasing β cell number primary amino acid sequence disclosed herein (such as SEQ ID NOs: 1-7) may result in polypeptides which have substantially equivalent activity as compared to the unmodified counterpart polypeptide described herein. Such modifications may be deliberate, for example as by site-directed mutagenesis (for example, introducing non-naturally occurring changes to the amino acid sequence or structure), or may be spontaneous. All of the polypeptides produced by these modifications are included herein. Thus, a specific, non-limiting example of an *Aeromonas* protein increasing β cell numbers is a conservative variant of the protein (such as a single conservative amino acid substitution, for example, one or more conservative amino acid substitutions, for example 1-10 conservative substitutions, 2-5 conservative substitutions, 4-9 conservative substitutions, such as 1, 2, 5 or 10 conservative substitutions). In other examples, the *Aeromonas* protein increasing β cell number may include one or more non-conservative substitutions (for example 1-10 non-conservative substitutions, 2-5 non-conservative substitutions, 4-9 non-conservative substitutions, such as 1, 2, 5 or 10 non-conservative substitutions), so long as the protein retains an activity of increasing β cell number in the pancreas.

In additional embodiments, the protein includes a tag (such as an N-terminal or C-terminal tag), for example for use in protein purification. One of skill in the art can select appropriate tags, such as a His-tag, a GST tag, or an antibody recognition sequence (such as a Myc-tag or HA-tag). In some examples, the tag is removed prior to us (for example, prior to administration to a subject). The protein can also be produced as a fusion protein, either to facilitate expression and/or purification or to facilitate delivery to a subject. For example, fusion proteins including a therapeutic molecule (such as the disclosed proteins) and transferrin has been shown to be useful for oral delivery routes. In other examples, the disclosed proteins may include a detectable label, such as a radioisotope, fluorophore, or hapten.

In some embodiments, the *Aeromonas* protein increasing β cell number is encoded by a nucleic acid sequence which includes, consists essentially of, or consists of the nucleic acid sequence set forth as SEQ ID NOs: 8-10. In additional embodiments, a nucleic acid encoding an *Aeromonas* protein increasing β cell number disclosed herein has at least 50%, 55%, 60%, 65%, 70%, 75%, 80%, 85%, 90%, 95%, 96%, 97%, 98%, or 99% sequence identity to the nucleic acid sequence set forth in SEQ ID NOs: 8-10 or a fragment thereof. In some examples, the nucleic acid has a nucleic acid sequence with at least 50%, 55%, 60%, 65%, 70%, 75%, 80%, 85%, 90%, 95%, 96%, 97%, 98%, 99%, or 100% sequence identity to a nucleic acid encoding a portion of a protein increasing β cell number, such as encoding the SYLF domain, for example corresponding to amino acids 114-258 of SEQ ID NOs: 1-3 (such as corresponding to nucleotides 340-774 of SEQ ID NOs: 8-10) or encoding a mature (processed) form of the protein (such as corresponding to nucleotides 64-786 of SEQ ID NO: 8). Exemplary sequences can be obtained using computer programs that are readily available on the internet and the nucleic acid and amino acid sequences set forth herein. In some examples, the nucleic acid encodes a polypeptide that retains a function of the protein, such as increasing the number of β cells and/or reducing or inhibiting one or more signs or symptoms of diabetes in a subject.

Exemplary *Aeromonas* nucleic acids encoding the disclosed proteins include SEQ ID NOs: 8-10 and the nucleic acid sequences of GenBank Accession Nos. NZ_ATFB01000020 (nucleotides 294943 . . . 295728) (SEQ ID NO: 8), CP002607 (nucleotides 1210185 . . . 1210970), NZ_ALOT01000039 (complement7714 . . . 8499), NZ_JMGO01000024 (nucleotides 4145 . . . 4924), and NZ_AOTK01000020 (complement 37734 . . . 38510); all of which are incorporated herein by reference in their entirety as present in GenBank on Sep. 22, 2014.

Additional nucleic acids encoding proteins increasing β cell number include nucleic acids with at least 50% (such as at least 55%, 60%, 65%, 70%, 75%, or more identity) sequence identity to SEQ ID NOs: 8-10 or at least 20% (such as at least 30%, 40%, 50%, 60%, 70%, 80%, or more identity) to a fragment of SEQ ID NOs: 8-10, such as the SYLF domain (e.g., corresponding to nucleotides 340-774 of SEQ ID NOs: 8-10) or a mature (processed) form of the protein (such as corresponding to nucleotides 64-786 of SEQ ID NO: 8). An additional exemplary additional nucleic acid includes, consists essentially of, or consists of SEQ ID NO: 11. In some examples, the nucleic acid sequences include those of GenBank Accession Nos. NZ_AMZO01000030 (nucleotides 1616 . . . 2386) and BBMN01000001 (nucleotides 356894 . . . 357667) (*Photobacterium*) or NZ_AWMU01000020 (complement of nucleotides 20075 . . . 20854) and INTF01000013 (nucleotides 123187 . . . 123966) (*Vibrio*), NZ_KI535451 (complement of nucleotides 317490 . . . 318077, *Klebsiella*), and ACOV01006014 (*Enterococcus gallinarum*), all of which are incorporated herein by reference in their entirety as present in GenBank on May 27, 2015. One of ordinary skill in the art can identify additional nucleic acids increasing β cell number related to the proteins disclosed herein, for example from other microbiota.

Minor modifications of nucleic acids encoding a protein increasing β cell number primary amino acid sequence (such as SEQ ID NOs: 8-11) are also contemplated herein. Such modifications to the nucleic acid may result in polypeptides that have substantially equivalent activity as compared to the unmodified counterpart polypeptide described herein. Such modifications may be deliberate, for example as by site-directed mutagenesis, or may be spontaneous. All of the nucleic acids produced by these modifications are included herein. Thus, a specific, non-limiting example of modified nucleic acid encoding protein increasing β cell number is a nucleic acid encoding conservative variant of the protein (such as a single conservative amino acid substitution, for example, one or more conservative amino acid substitutions, for example 1-10 conservative substitutions, 2-5 conservative substitutions, 4-9 conservative substitutions, such as 1, 2, 5 or 10 conservative substitutions). In other examples, the nucleic acid may encode a protein including one or more non-conservative substitutions (for example 1-10 non-conservative substitutions, 2-5 non-conservative substitutions, 4-9 non-conservative substitutions, such as 1, 2, 5 or 10 non-conservative substitutions), so long as the encoded protein retains activity that increases β cell number or β cell proliferation.

In some examples, the nucleic acid encoding the protein increasing β cell number is codon-optimized for the cell in which it is to be expressed. Codon usage bias, the use of synonymous codons at unequal frequencies, is ubiquitous among genetic systems (Ikemura, *J. Mol. Biol.* 146:1-21, 1981; Ikemura, *J. Mol. Biol.* 158:573-97, 1982). The strength and direction of codon usage bias is related to genomic G+C content and the relative abundance of different iso accepting tRNAs (Akashi, *Curr. Opin. Genet. Dev.* 11:660-6, 2001; Duret, *Curr. Opin. Genet. Dev.* 12:640-9, 2002; Osawa et al., *Microbiol. Rev.* 56:229-64, 1992). Codon usage can affect the efficiency of gene expression. For example, in *Escherichia coli* (Ikemura, *J. Mol. Biol.* 146:1-21, 1981; Xia Genetics 149:37-44, 1998) the most highly expressed genes use codons matched to the most abundant tRNAs (Akashi and Eyre-Walker, *Curr. Opin. Genet. Dev.* 8:688-93, 1998).

Codon-optimization refers to replacement of a codon in a nucleic acid sequence with a synonymous codon (one that codes for the same amino acid) more frequently used (preferred) in the organism. Each organism has a particular codon usage bias for each amino acid, which can be determined from publicly available codon usage tables (for example see Nakamura et al., *Nucleic Acids Res.* 28:292, 2000 and references cited therein). For example, a codon usage database is available on the World Wide Web at kazusa.or.jp/codon. One of skill in the art can modify a nucleic acid encoding a particular amino acid sequence, such that it encodes the same amino acid sequence, while being optimized for expression in a particular cell type (such as a bacterial or mammalian cell). However, one of skill in the art will recognize that a nucleic acid does not have to be optimized for expression in a particular organism in order to be used for gene expression in the selected organism.

In additional embodiments, the nucleic acid encoding the protein increasing β cell number further includes a nucleic acid sequence encoding a tag (such as an N-terminal or C-terminal tag), for example for use in protein purification. One of skill in the art can select nucleic acids encoding appropriate tags, such as a His-tag, a GST tag, or an antibody recognition sequence (such as a Myc-tag or HA-tag). The nucleic acid may also encode a fusion, for example, a nucleic acid encoding a fusion protein including a disclosed protein and transferrin. In other examples, the disclosed nucleic acids may include a detectable label, such as a radioisotope, fluorophore, or hapten.

Nucleic acid molecules encoding a protein increasing β cell number disclosed herein also include a recombinant DNA which is incorporated into a vector, into an autonomously replicating plasmid or virus, or into the genomic DNA of a prokaryote or eukaryote, or which exists as a separate molecule (such as a cDNA) independent of other sequences. A nucleic acid encoding a protein increasing β cell number (such as a nucleic acid encoding a protein increasing β cell number, for example any one of SEQ ID NOs: 8-11 or a fragment thereof) is in some examples operatively linked to heterologous expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (e.g., ATG) in front of a protein-encoding nucleic acid, splicing signal for introns, maintenance of the correct reading frame of that gene to permit proper translation of mRNA, and stop codons. The expression control sequence(s) in some examples are heterologous expression control sequence(s), for example from an organism or species other than the protein-encoding nucleic acid. Thus, the protein-encoding nucleic acid operably linked to a heterologous expression control sequence (such as a promoter) comprises a nucleic acid that is not naturally occurring. In other examples, the nucleic acid is operably linked to a tag sequence (such as 6× His, HA tag, or Myc tag) or another protein-coding sequence, such as glutathione S-transferase or maltose binding protein.

Vectors for cloning, replication, and/or expression of the disclosed nucleic acid molecules include bacterial plasmids, such as bacterial cloning or expression plasmids (some of which can be used for expression in bacterial and/or mammalian cells). Exemplary bacterial plasmids into which the nucleic acids can be cloned include *E. coli* plasmids, such as pBR322, pUC plasmids (such as pUC18 or pUC19), pBluescript, pACYC184, pCD1, pGEM® plasmids (such as pGEM®-3, pGEM®-4, pGEM-T® plasmids; Promega, Madison, Wis.), TA-cloning vectors, such as pCR® plasmids (for example, pCR® II, pCR® 2.1, or pCR® 4 plasmids; Life Technologies, Grand Island, N.Y.) or pcDNA plasmids (for example pcDNA™ 3.1 or pcDNA™ 3.3 plasmids; Life Technologies). In some examples, the vector includes a heterologous promoter which allows protein expression in bacteria. Exemplary vectors include pET vectors (for example, pET-21b), pDEST™ vectors (Life Technologies), pRSET vectors (Life Technologies), pBAD vectors, and pQE vectors (Qiagen). The disclosed nucleic acids can be also be cloned into *B. subtilis* plasmids, for example, pTA1060 and pHT plasmids (such as pHT01, pHT43, or pHT315 plasmids). One of skill in the art can select additional vectors suitable for cloning and/or bacterial or mammalian expression of proteins increasing (cell number such as those disclosed herein.

In other embodiments, vectors are used for expression in yeast such as *S. cerevisiae* or *Kluyveromyces lactis*. Several promoters are known to be of use in yeast expression systems such as the constitutive promoters plasma membrane $H^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, many inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (2μ) or single copy (CEN) plasmids to give an additional level of control in expression level. The plasmids can include nutritional markers (such as URA3, ADE3, HIS1, and others) for selection in yeast and antibiotic resistance (such as AMP) for propagation in bacteria. Plasmids for expression on *K. lactis* are known, such as pKLAC1. Thus, in one example, after amplification in bacteria, plasmids can be introduced into the corresponding yeast auxotrophs by methods similar to bacterial transformation.

Viral vectors including the disclosed polynucleotides (such as polynucleotides encoding a protein increasing β cell number) can also be prepared. A number of viral vectors have been constructed, including polyoma, SV40 (Madzak et al., 1992, *J. Gen. Virol.,* 73:15331536), adenovirus (Berkner, 1992, *Curr. Top. Microbiol. Immunol.,* 158:39-6; Berliner et al., 1988, *BioTechniques,* 6:616-629; Gorziglia et al., 1992, *J. Virol.,* 66:4407-4412; Quantin et al., 1992, *Proc. Natl. Acad. Sci. USA,* 89:2581-2584; Rosenfeld et al., 1992, *Cell,* 68:143-155; Wilkinson et al., 1992, *Nucl. Acids Res.,* 20:2233-2239; Stratford-Perricaudet et al., 1990, *Hum. Gene Ther.,* 1:241-256), vaccinia virus (Mackett et al., 1992, *Biotechnology,* 24:495-499), adeno-associated virus (Muzyczka, 1992, *Curr. Top. Microbiol. Immunol.,* 158:91-123; On et al., 1990, *Gene,* 89:279-282), herpes viruses including HSV and EBV (Margolskee, 1992, *Curr. Top. Microbiol. Immunol.,* 158:67-90; Johnson et al., 1992, *J. Virol.,* 66:2952-2965; Fink et al., 1992, *Hum. Gene Ther.* 3:11-19; Breakfield et al., 1987, *Mol. Neurobiol.,* 1:337-371; Fresse et al., 1990, *Biochem. Pharmacol.,* 40:2189-2199), Sindbis viruses (Herweijer et al., 1995, *Hum. Gene Ther.* 6:1161-1167; U.S. Pat. Nos. 5,091,309 and 5,2217,879), alphaviruses (S. Schlesinger, 1993, *Trends Biotechnol.* 11:18-22; Frolov et al., 1996, *Proc. Natl. Acad. Sci. USA* 93:11371-11377) and retroviruses of avian (Brandyopadhyay et al., 1984, *Mol. Cell Biol.,* 4:749-754; Petropouplos et al., 1992, *J. Virol.,* 66:3391-3397), murine (Miller, 1992, *Curr. Top. Microbiol. Immunol.,* 158:1-24; Miller et al., 1985, *Mol. Cell Biol.,* 5:431-437; Sorge et al., 1984, *Mol. Cell Biol.,* 4:1730-1737; Mann et al., 1985, *J. Virol.,* 54:401-407), and human origin (Page et al., 1990, *J. Virol.,* 64:5370-5276; Buchschalcher et al., 1992, *J. Virol.,* 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

DNA sequences encoding a protein increasing β cell number can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Host cells can include microbial, yeast, insect and mammalian host cells. Methods of expressing DNA sequences having eukaryotic or viral sequences in prokaryotes are well known in the art. Non-limiting examples of suitable host cells include bacteria, Archaea, insect, fungi (for example, yeast), mycobacterium (such as *M. smegmatis*), plant, and animal cells (for example, mammalian cells, such as human). Exemplary cells of use include *E. coli, Bacillus subtilis, Saccharomyces cerevisiae, Salmonella typhimurium,* SF9 cells, C129 cells, 293 cells, *Neurospora,* and immortalized mammalian myeloid and lymphoid cell lines. Techniques for the propagation of mammalian cells in culture are well-known (see, Jakoby and Pastan (eds.), 1979, Cell Culture. *Meth. Enzymol.,* volume 58, Academic Press, Inc., Harcourt Brace Jovanovich, N.Y.). Examples of commonly used mammalian host cell lines are VERO and HeLa cells, CHO cells, and WI38, BHK, and COS cell lines, although other cell lines may be used, such as cells designed to provide higher expression, desirable glycosylation patterns, or other features. As discussed above, techniques for the transformation of yeast cells, such as polyethylene glycol transformation, protoplast transformation and gene guns are also known in the art (see Gietz and Woods *Meth. Enzymol.* 350: 87-96, 2002).

Transformation of a host cell with recombinant DNA can be carried out by conventional techniques as are well known to those skilled in the art. Where the host is prokaryotic, such as, but not limited to, *E. coli,* competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with a polynucleotide encoding a protein increasing β cell number (or a portion or fragment thereof) and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Eukaryotic Viral Vectors, Cold Spring Harbor Laboratory, Gluzman ed., 1982).

IV. Methods of Increasing Pancreatic β Cells

Disclosed herein are methods of increasing pancreatic β cell proliferation or number. In some embodiments, the methods include contacting pancreatic β cells with an effective amount of a protein increasing β cell number (such as a protein with at least 80% sequence to any one of SEQ ID NOs: 1-7 or a fragment thereof), including, but not limited to the proteins disclosed herein, cells producing the protein, a cell extract, or a preparation (such as a cell-free supernatant) from a cell producing the protein, an isolated or purified protein increasing β cell number (including, but not limited to a polypeptide with at least 80% sequence identity to any one of SEQ ID NOs: 1-7 or a fragment thereof), or a nucleic acid encoding a protein increasing β cell number (including, but not limited to, nucleic acids with at least 80% sequence identity to any one of SEQ ID NOs: 8-11 or a fragment thereof). In some examples, contacting pancreatic β cells with the protein or other preparation includes administering the preparation to a subject, for example, a subject with diabetes.

Also disclosed are methods of treating or inhibiting diabetes in a subject. In some embodiments, the methods include administering to a subject an effective amount of a protein increasing β cell number (such as an *Aeromonas* protein increasing β cell number, such as a protein with at least 80% sequence to any one of SEQ ID NOs: 1-7 or a fragment thereof), including, but not limited to the proteins disclosed herein. The protein increasing β cell number may be administered in any form, including administration of cells producing a protein increasing β cell number disclosed herein (e.g., *A. veronii* or other bacteria recombinantly expressing or overexpressing a protein increasing β cell number), a cell extract, or a preparation (such as a cell-free supernatant) from a cell producing a protein increasing β cell number, an isolated or purified protein increasing β cell number (including, but not limited to a protein with at least 80% sequence to any one of SEQ ID NOs: 1-7 or a fragment thereof), or a nucleic acid encoding a protein increasing β cell number (including, but not limited to, a nucleic acid with at least 80% sequence to any one of SEQ ID NOs: 8-11 or a fragment thereof). In particular embodiments, the subject is a subject with type I diabetes.

The proteins disclosed herein can be chemically synthesized by standard methods, or can be produced recombinantly. An exemplary process for polypeptide production is described in Lu et al., *FEBS Lett.* 429:31-35, 1998. They can also be isolated by methods including preparative chromatography and immunological separations. Polypeptides can also be produced using molecular genetic techniques, such as by inserting a nucleic acid encoding a protein increasing β cell number or a portion thereof into an expression vector, introducing the expression vector into a host cell (such as *E. coli*), and isolating the polypeptide (for example, as discussed in Section III). In some examples, the protein includes a tag (such as an N-terminal or C-terminal tag), for example for use in protein purification. One of skill in the art can select appropriate tags, such as a His-tag, a GST tag, or an antibody recognition sequence (such as a Myc-tag or HA-tag).

In some embodiments, the protein increasing β cell number (such as a protein comprising the sequence of any one of SEQ ID NOs: 1-7 or a protein that is at least 50%, 55%, 60%, 65%, 70%, 75%, 80%, 85%, 90%, 95%, 98%, or 99% identical to any one of SEQ ID NOs: 1-7 or a fragment thereof) is administered to a subject to treat or inhibit diabetes. In some examples, a fragment of the protein includes the processed mature protein (for example, a protein lacking the putative secretion signal sequence corresponding to amino acids 1-21 of SEQ ID NO: 1) or a domain of the protein (such as a SYLF domain, for example a domain corresponding to amino acids 114-258 of any one of SEQ ID NOs: 1-3). In particular embodiments, the subject has type I diabetes.

The cells, cell extract, protein increasing β cell number, or nucleic acid encoding the protein increasing β cell number can be administered to a subject in need of treatment using any suitable means known in the art. Methods of administration include, but are not limited to, intradermal, intramuscular, intraperitoneal, parenteral, subcutaneous, rectal, intranasal, inhalation, oral, or by gene gun. Intranasal administration refers to delivery of the compositions into the nose and nasal passages through one or both of the nares and can include delivery by a spraying mechanism or droplet mechanism, or through aerosolization of the therapeutic agent. In particular examples, the protein increasing β cell number, nucleic acid encoding the protein, or a preparation including the protein (such as a cell extract or preparation of cells expressing the protein) is administered orally. In other examples, the protein increasing β cell number, nucleic acid encoding the protein, or a preparation including the protein (such as a cell extract or preparation of cells expressing the protein) is administered subcutaneously or intramuscularly.

Therapeutic agents can be administered in any suitable manner, for example, with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure. Pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of one or more therapeutic agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Compositions for oral administration include powders or granules, suspensions or solutions in water or non-aqueous media, capsules, sachets, or tablets. Thickeners, flavorings, diluents, emulsifiers, dispersing aids or binders may be desirable.

The amount of protein increasing β cell number, nucleic acid encoding the protein increasing (3 cell number, or a preparation including the protein increasing β cell number (such as a cell extract or preparation of cells expressing the protein) to be administered to a subject can be selected by one of ordinary skill in the art, for example from about 1 μg to 5 g of the protein increasing β cell number (such as about 10 μg to 1 g, 100 μg to 500 mg, or 1 mg to 100 mg). In other examples, the amount of protein increasing β cell number or a preparation including the protein (such as a cell extract or preparation of cells expressing the protein) to be administered to a subject is about 0.001 mg/kg to about 1000 mg/kg (such as about 0.01 mg/kg to about 500 mg/kg, about 1 mg/kg to about 250 mg/kg, or about 10 mg/kg to 100 mg/kg).

The dosage can be administered one or more times per day, in divided doses (such as 2, 3, or 4 divided doses per day), or in a single dosage daily. The dosage can also be administered every 2 days, every 3 days, bi-weekly, once weekly, semi-weekly, or monthly. In some examples, an effective amount of protein increasing β cell number protein or nucleic acid encoding the protein or a cell-extract or preparation of cells expressing the protein is an amount that inhibits or ameliorates one or more symptoms of diabetes (for example, decreases blood glucose levels or increases insulin production). In other examples, an effective amount is an amount that increases β cell number in a subject (for example, compared to a control or compared to the subject prior to administration of the protein increasing β cell number or preparation).

In particular examples, prior to, during, or following administration of a disclosed protein increasing β cell number (or nucleic acid encoding the protein, or preparation of cells expressing the protein or cell-free extract including the protein) the subject can receive one or more other therapies. Examples of such therapies include, but are not limited to, lifestyle modifications (such as diet and exercise), insulin, metformin, sulfonylureas (such as glyburide, glipizide, or glimepiride), meglitinides (such as repaglinide or nateglinide), thiazolidinediones (such as rosiglitazone or pioglitazone), DPP-4 inhibitors (such as sitagliptin, saxagliptin, or linagliptin), GLP-1 receptor agonists (such as exenatide or liraglutide), and SGLT2 inhibitors (such as canagliflozin or dapagliflozin). Combinations of one or more of these therapies can also be administered to a subject.

V. Methods of Identifying Proteins that Increase β Cell Number

Disclosed herein are methods for identifying modulators of β cell number (such as proliferation, specification, and/or survival), for example, proteins that increase β cell number and/or stimulate β cell proliferation. In some embodiments, the methods include inoculating germ-free zebrafish (or a population of germ-free zebrafish) with one or more defined bacterial strains or CFS supernatant from one or more defined bacterial strains and/or one or more test compounds and determining the number of β cells or β cell proliferation, or a marker of β cell number or proliferation (such as glucose or insulin levels) in the zebrafish. In some examples, the zebrafish are transgenic for one or more genes, for example, are transgenic for green fluorescent protein (GFP) or another visibly or otherwise readily detectable protein expressed under the control of the insulin promoter. In other embodiments, the methods include inoculating conventionally raised zebrafish (or a population of conventionally raised zebrafish) with one or more test compounds and determining the number or proliferation of β cells or a marker of β cell number or proliferation (such as glucose or insulin levels).

In some examples, the number of β cells in a fish is determined. Presence or amount of β cells in the pancreas can be determined by histological staining, in situ hybridization, flow cytometry, or immunohistochemistry. In one particular example, presence or amount of β cells is determined by detection of a marker expressed under the control of a neutrophil-specific gene (such as green fluorescent protein (GFP) expressed from the insulin promoter, as described below). In other examples, presence or amount of β cells is determined by detection of one or more proteins expressed by β cells (for example, specifically expressed by β cells but not by other pancreatic cells), such as insulin, diacylglycerol kinase beta (DGKB), or glycoprotein M6A (GPM6A) (see, e.g., Dorrell et al., *Mol. Cell. Endocrinol.* 339:144-150, 2011). One of ordinary skill in the art can identify additional markers for detection of presence and/or amount of β cells.

In some examples, the number of β cells or the amount of proliferation of β cells in a zebrafish contacted or treated with a bacterial strain, CFS from a bacterial strain, or other test compound is compared to a control. In some examples, the control is a zebrafish (or population of zebrafish) treated under the same conditions, but without treatment with the bacterial strain, CFS, or test compound. Bacterial strains or test compounds identified as modulating β cell number and/or proliferation may be selected for further testing. If the modulator is a bacterial strain, additional testing may be carried out to identify or purify one or more β cell number increasing compounds from the bacteria Bacterial strains that may be used in the screening methods disclosed herein (either for inoculation of germ-free zebrafish or for preparing CFS with which the zebrafish are contacted) include, but are not limited to *Aeromonas, Shewanella, Photobacterium, Acinetobacter, Pseudomonas, Variovorax, Vibrio, Enterobacter, Plesiomonas,* and *Delftia*. Additional bacterial strains, such as additional strains found in the zebrafish or mammalian gut (such as the human gut), for example *Enterococcus, Klebsiella, Enterobacter,* or *Escherichia,* can also be tested for the ability to increase β cell number or stimulate β cell proliferation in the methods disclosed herein.

A "compound" or "test compound" is any substance or any combination of substances that is useful for achieving an end or result. Any compound that has potential (whether or not ultimately realized) to modulate β cell number and/or proliferation can be tested using the methods of this disclosure.

Exemplary compounds include, but are not limited to, peptides, such as soluble peptides, including but not limited to members of random peptide libraries (see, e.g., Lam et al., *Nature,* 354:82-84, 1991; Houghten et al., *Nature,* 354:84-86, 1991), and combinatorial chemistry-derived molecular libraries made of D- and/or L-configuration amino acids, phosphopeptides (including, but not limited to, members of random or partially degenerate, directed phosphopeptide libraries; see, e.g., Songyang et al., *Cell,* 72:767-778, 1993), antibodies (including, but not limited to, polyclonal, monoclonal, humanized, anti-idiotypic, chimeric or single chain antibodies, and Fab, $F(ab')_2$. and Fab expression library fragments, and epitope-binding fragments thereof), small organic or inorganic molecules (such as, so-called natural products or members of chemical combinatorial libraries), molecular complexes (such as protein complexes), or nucleic acids (such as antisense compounds).

Appropriate compounds can be contained in libraries, for example, synthetic or natural compounds in a combinatorial library. Numerous libraries are commercially available or can be readily produced; means for random and directed synthesis of a wide variety of organic compounds and biomolecules, including expression of randomized oligonucleotides, such as antisense oligonucleotides and oligopeptides, also are known. Alternatively, libraries of natural compounds in the form of bacterial, fungal, plant and animal extracts are available or can be readily produced. Additionally, natural or synthetically produced libraries and compounds are readily modified through conventional chemical, physical and biochemical means, and may be used to produce combinatorial libraries. Such libraries are useful for the screening of a large number of different compounds.

In some examples, the number of β cells is measured by counting the number of β cells in the pancreas (such as the exocrine pancreas) of a subject. Methods for counting β cells include manual counting (for example examining a sample (such as tissue or an organism under a microscope) and counting the number of β cells. β cells can be identified by staining techniques, including histological stains (such as hematoxylin and eosin) and immunohistochemistry or in situ hybridization (for example, using β cell-specific antibodies or probes (such as for insulin, diacylglycerol kinase beta, or glycoprotein M6A)). In other examples, the number of β cells is measured using a label that is expressed under the control of a neutrophil-specific promoter (such as transgenic zebrafish expressing green fluorescent protein (GFP) under the control of the insulin promoter; see, e.g., diIorio et al., *Dev. Biol.* 244:75-84, 2002). An increase in the number of β cells (such as an increase of at least about 10%, about 20%, about 50%, about 80%, about 90%, about 1.5-fold, about 2-fold, about 3-fold, about 5-fold, about 10-fold or more) in mono-associated zebrafish in the presence of one or more bacterial strains or test compounds as compared to in the absence of the one or more bacterial strains or test compounds indicates that the compound increases β cell number and/or proliferation.

In other examples, β cell proliferation is measured. Methods of measuring cell proliferation are known to one of ordinary skill in the art. Such methods include in vitro or in vivo methods. In some examples, cell proliferation is measured by incorporation of a DNA label (for example 5-bromo-2-deoxyuridine (BrdU), 5-ethynyl-2'-deoxyuridine, (EdU) or [$^3$H]thymidine). In the presence of label, cells which are in S-phase incorporate the label. After an incubation period, cells which were in S-phase during the labeling period can be detected, such as by autoradiography (for cells labeled with [$^3$H]thymidine) or with fluorescently-labeled antibodies specific to BrdU (for cells labeled with BrdU), or appropriate detection reagents (for EdU, such as CLICK-IT EdU kit, Invitrogen). An increase in the number of labeled cells (such as an increase of about 10%, about 20%, about 50%, about 80%, about 90%, about 1.5-fold, about 2-fold, about 3-fold, about 5-fold, about 10-fold or more) in the presence of one or more bacterial strains, CFS, and/or test compounds as compared to in the absence of the bacterial strains, CFS, and/or test compounds indicates that the compound increases β cell proliferation.

In other examples, β cell proliferation is measured by detecting cellular DNA content in a population of cells, as DNA content is closely proportional to cell number. Such methods include detecting a dye that binds to nucleic acids (such as CYQUANT cell proliferation kit, Invitrogen). In other examples, cell proliferation is measured by quantifying cleavage of a tetrazolium salt (such as MTT, XTT, or MTS) to insoluble formazan crystals by mitochondrial dehydrogenase.

In additional examples, β cell proliferation is measured using a transgenic zebrafish line that mark proliferating and quiescent β cells (see, e.g., Tsuji et al., *PLoS ONE* 9(8): e104112, 2014). One of ordinary skill in the art can identify additional methods to measurer β cell proliferation.

Glucose levels in zebrafish correlate with the number and/or proliferation of β cells. Therefore, in still further examples, the effect of a bacterial strain, CFS, and/or test compound on number and/or proliferation of β cells can be determined by measuring glucose levels in zebrafish treated with the bacterial strains, CFS, and/or test compounds as compared to zebrafish in the absence of the bacterial strains, CFS, and/or test compounds.

The following examples are provided to illustrate certain particular features and/or embodiments. These examples should not be construed to limit the disclosure to the particular features or embodiments described.

Example 1

Materials and Methods

Gnotobiotic zebrafish: All experiments with zebrafish were performed using protocols approved by the University of Oregon Institutional Care and Use Committee and followed standard protocols. Zebrafish embryos were derived germ-free (GF) as previously described (Milligan-Myhre et al., *Meth. Cell Biol.* 105:87-116, 2011). XGF and mono-associated larvae were also generated as previously described (Bates et al., *Dev. Biol.* 297:374-386, 2006), except that all bacterial inoculums were added to the GF flasks at 4 days post fertilization (dpf) at a final concentration of $10^6$ colony forming units (CFU)/mL. In experiments quantifying the colonization levels of bacterial isolates, each strain was added directly to the water and allowed to incubate with the larvae for 48 hours at 37° C. At 6 dpf the fish were sacrificed before the gut was removed and homogenized in a small sample of sterile embryo medium (EM). Dilutions of this gut slurry were plated onto tryptic soy agar and allowed to incubate overnight at 30° C. Colonies from each gut were quantified and a minimum of 10 guts per mono-association were analyzed.

Free Glucose Assay: To measure β cell function in GF and CV zebrafish larvae, levels of free glucose were measured at 6 dpf using a free glucose assay kit (BioVision) as described previously (Gut et al., *Nat. Chem. Biol.* 9:97-104, 2013), except that only 10 larvae were combined per tube. Three to five biological replicates were completed for both GF and CV treatments each time the assay was conducted. Data represented herein have been combined from three separate experimental assays.

Cell Free Supernatant: Secreted bacterial products were inoculated to GF fish at 4 dpf by adding cell free supernatant (CFS) at a final concentration of 500 ng/mL to the water of the sterile flasks. CFS was harvested from a 50 mL overnight culture of the specified bacterial strain. The cultures were centrifuged at 7000×g for 10 minutes at 4° C. Subsequently, the supernatant was filtered through a 0.22-μm sterile tube-top filter (Corning Inc., NY). The sterile supernatant was concentrated at 4° C. for 1 hour at 3000×g with a centrifugal device that has a 10 kDa weight cut off (Pall Life Sciences). For experiments utilizing proteinase K (Qiagen), the enzyme was added to samples of CFS at a final concentration of 100 μg/mL and allowed to incubate at 55° C. for 1 hour before inactivating the enzyme at 90° C. for 10 minutes.

Ammonium Sulfate Fractionation: Ammonium sulfate fractionation was performed on un-concentrated, sterile CFS from a 50 mL overnight culture by slowly adding 100% ammonium sulfate until solutions of 20%, 40%, 60% or 80% ammonium sulfate were achieved. These solutions were prepared at 4° C. Precipitated proteins were collected from each fraction by centrifugation at 4° C. and 14000 s g for 15 minutes. The proteins were resuspended in cold embryo medium and dialyzed for 2-3 hours at 4° C. before adding them to GF larvae age 4 dpf at a final concentration of 500 ng/mL.

Mass Spectrometry: The 60-80% ammonium sulfate fraction of the *A. veronii*$^{\Delta T2SS}$ CFS, frozen in liquid nitrogen, were sent to the Proteomics Lab at Oregon Health and Sciences University in Portland, Oreg. for protein identification (partial sequencing) analysis.

Figure 4A:
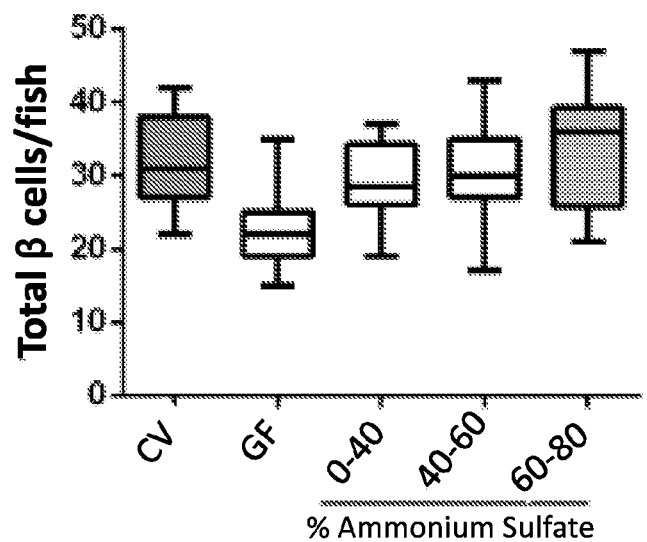
FIGS. 4A and 4B are panels showing fractionation of *A. veronii* CFS.
Figure 4B:
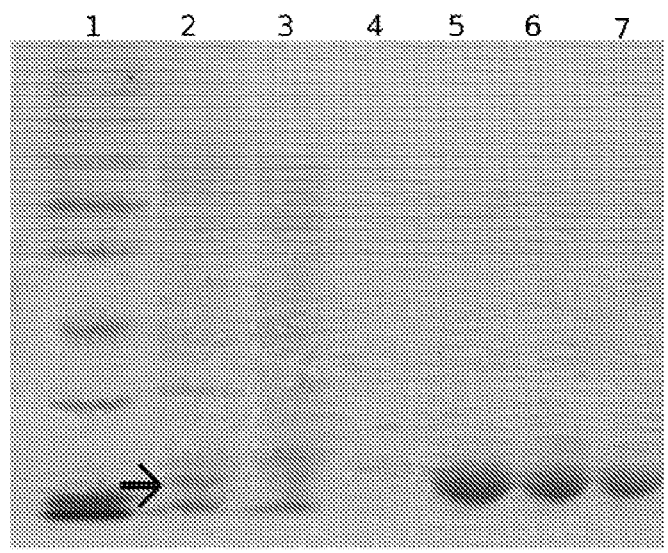

BefA purification: The nucleotide sequence for the befA gene was amplified from *A. veronii* using the following forward and reverse PCR primers respectively: 5'-GC-CCATATGatgaacaagcgtaactggttgctg-3' (SEQ ID NO: 12) and 5'-GGCCTCGAGgcggctcgtttcagtcaagtc-3' (SEQ ID NO: 13). The amplified fragment was then cloned into the pET-21b plasmid (Novagen) which contained an IPTG inducible promoter. A His tag was added to the C-terminal of the protein sequence for subsequent purification. This vector was transformed into the BL21 *Escherichia coli* strain, and treated with 0.1 mM IPTG during early exponential growth phase ($OD_{600}$=0.4-0.6) and allowed to grow for 3-4 more hours at 30° C. This resulted in a supernatant dominated by BefA, as confirmed via SDS-page gel electrophoresis by the presence of a dark band of the expected size of BefA, 29 kDa. This band was absent from BL21 cultures carrying an empty pET-21b vector. IPTG-induced BL21 cells were sonicated at 32,000×g in a 50 nM Tris, 150 mM NaCl buffer (buffer A). The supernatant was then added to a solution of nickel beads (Thermo Scientific HisPur™ Ni-NTA Resin) to capture the His tag. The beads were washed three times for 15 minutes in a 20 mM imidazole solution and subsequently eluted in a 500 mM imidazole solution. The isolation of pure BefA was confirmed with SDS-page gel electrophoresis by the presence of a single band of about 29 kDa in size (FIG. 4B). Purified BefA was added to 4 dpf GF fish at a final concentration of 500 ng/mL.

Experimental bacterial strains: To create the *A. veronii*$^{\Delta befA}$ mutant strain, a vector containing a chloramphenicol resistance cassette was transformed into SM10 *E. coli*. Conjugation between wild type *Aeromonas veronii* HM21 and the vector carrying SM10 *E. coli* strain was carried out, allowing for the chloramphenicol resistance gene to replace the befA locus via allelic exchange in *A. veronii* cells that received the vector. Candidates were selected for loss of the plasmid and maintenance of chloramphenicol resistance. The insertion of the chloramphenicol cassette into the befA locus was verified in these candidates by PCR. The *A. veronii*$^{\Delta T2SS}$ strain was provided by Joerg Graf.

β cell quantification and EdU staining: Tg(−1.0insulin:eGFP)[14] zebrafish embryos were used to visualize and quantify the total number of β cells in the developing larvae. All experiments were analyzed at 6 dpf unless otherwise specified. For experiments quantifying the proliferation, EdU was added at 4 dpf directly to the EM at a final concentration of 0.1 mg/mL. At all time points and experiments, larvae were fixed with 4% paraformaldehyde at 4° C. overnight and then washed with 1× PBS. The Click-iT® EdU Imaging Kit (Invitrogen) was used to process the EdU label in whole fixed zebrafish, except when quantifying IEC proliferation when fish were sectioned first, according to the manufacturer's protocols. Finally, larvae were also stained with rabbit anti-GFP (Life Technologies), Alexa Fluor® 488 goat anti-rabbit (Jackson) and TO-PRO®-3-Iodide (642/661). Whole stained larvae were mounted for confocal microscopy (BioRad) with their right side facing up against the cover slip, which was flattened sufficiently to disrupt the islet for optimal resolution of individual cells. For quantification of β cells, the entire endocrine portion of the pancreas was scanned through using a 60× objective, and FIJI software was used to analyze each image stack. For quantification of pancreatic exocrine tissue proliferation, Tg(ptf1a:eGFP)[31] zebrafish were scanned through the entire pancreas with a 20× objective and FIJI was used to analyze the percentage of proliferative cells in single sections from the center of the organ.

Cell culture: Cell lines, mouse insulinoma 13-TC-6 (ATCC® CRL-11506™) and rat small intestinal epithelia IEC-6 (ATCC® CRL-1592™), were cultured in standard conditions and in DMEM supplemented with 10% FBS. For β-TC-6 cells, low glucose (5 mM) DMEM was used and for the IEC-6 cells, medium was additionally supplemented with 0.1 Units/mL of bovine insulin. Media was changed every 48 hours and cells were split every 7 to 9 days. For experiments, cells were split into wells containing poly-D-lysine coated cover slips. They were allowed to recover for 24 hours before adding BefA and EdU at concentrations of 500 ng/mL and 10 µM, respectively. Cells were incubated with EdU and BefA or a control for 5 hours before the media was removed and the cells were fixed in 4% PFA for 15 minutes at room temperature. Cells were washed three times with PBS before developing the EdU signal according to the manufacturer's protocols. Cells were additionally stained with rabbit anti-insulin (Cell Signaling Cat #4590), Alexa Fluor 488 goat anti-rabbit (Jackson) and DAPI before being imaged using a confocal microscope (BioRad) with a 20× objective. A minimum of 1,000 β-TC-6 cells or 300 IEC-6 cells was quantified per cover slip and the software FIJI was used to analyze each image.

BefA phylogenetic analysis: BefA homologs were screened for across microbial species using a blastp-based search of the UniProt Knowledgebase (version 6/2015) (Altschul et al., *Nucl. Acids Res.* 17:3389-3402, 1997; UniProt Consortium, *Nucl. Acids Res.* 43:D204-212, 2015); default search parameters were changed to allow (i) a maximum E-value of 1.0 and (ii) an arbitrarily large number of database hits. Database hits were classified as "close homologs" if amino acid sequence identity exceeded 50% (relative to the query length) and as "distant homologs" if their percent identity exceeded 20%. For phylogenetic analysis at the species level, each species was represented by the hit of highest percent identity to BefA among isolates of that species (if any); an analogous procedure was used for genus-level analysis. Aligned portions of database sequences were isolated and multiply aligned with MUSCLE (Edgar, *Nucl. Acids Res.* 32:1792-1797, 2004). Phylogenetic trees were constructed from these multiple sequence alignments using PhyML (Guindon et al., *Syst. Biol.* 52:696-704, 2003) and visualized within the Phylogeny.fr webserver (Dereeper et al., *Nucl. Acids Res.* 36:W465-469, 2003). Microbial genera were classified as "human-associated" if they occurred with relative abundance >0.01% in at least 5 metagenomes from the Human Microbiome Project (Human Microbiome Project Consortium, *Nature* 486:207-214, 2012) as profiled by MetaPhlAn (Segata et al., *Nat. Meth.* 9:811-814, 2012).

Statistical Analysis: Each experiment was repeated multiple times, and data was analyzed through the statistical software R Studio. For experiments comparing just two differentially treated populations of larvae, a Student's t-test with equal variance assumptions was used. For experiments measuring a single variable (such as total β cells) with multiple treatment groups, a single factor ANOVA with post hoc means testing (Tukey) was utilized. A p-value of less than 0.05 was required to reject the null hypothesis that no difference existed between groups of data.

Example 2

Bacterial Protein that Induces Pancreatic β Cell Proliferation

This example describes identification and characterization of a bacterial protein that induces pancreatic β cell proliferation.

By 3 dpf, the larval zebrafish has developed a fully functional pancreas with a small population of newly differentiated insulin-secreting β cells (Field et al., *Dev. Biol.* 261:794-208, 2003; Kimmel et al., *Meth. Cell Biol.* 100:261-280, 2010). During the first week of development, these cells are tightly packed into the larvae's single islet, which can be readily visualized in transgenic fish expressing eGFP under the insulin promoter (diIorio et al., *Dev. Biol.* 244:75-84, 2002). From approximately 3 dpf onward, this population of β cells undergoes a linear expansion, matching the increasing metabolic demands of the growing larvae (Tsuji et al., *PLoS One* 9:e104112, 2014; Moro et al., *Dev. Biol.* 332:299-308, 2009). Both self-proliferation and neogenesis contribute to the growing β cell mass in the zebrafish (Hesselson et al., Proc. Natl. Acad. Sci. USA 106:14896-14901, 2009). At the outset of this expansion period, between 3 and 4 dpf, bacteria from the environment colonize the zebrafish intestine for the first time (Bates et al., Dev. Biol. 297:374-386, 2006). Human infants undergo a similar β cell expansion event, characterized by increased levels of proliferation (Gregg et al., J. Clin. Endocrinol. Metab. 97:3197-3206, 2012), which also occurs during initial establishment of the gut microbiota (Voreades et al., Front. Microbiol. 5:494, 2014).

To investigate a possible role for the microbiota in β cell expansion, total eGFP+ cells in germ free (GF) and conventionally reared (CV) Tg(-1.0insulin:eGFP) fish (diIorio et al., Dev. Biol. 244:75-84, 2002) at 3, 4, 5 and 6 dpf were quantified. The number of β cells in CV fish increased steadily from 3 to 6 dpf; however, the number of β cells in GF fish remained stagnant over this time (FIG. 1A). Furthermore, at 6 dpf, the overall structure of β cells within the primary islet of CV fish (FIG. 1B) appeared different from that of GF fish (FIG. 1C), with cells in the GF animals being less densely packed. β cell numbers were rescued to CV levels by the addition of non-sterile tank water to GF larvae by 4 dpf (FIG. 1D, XGF). These results suggested that development of a complete β cell population was dependent upon microbes or microbial-derived products.

Figure 1E:
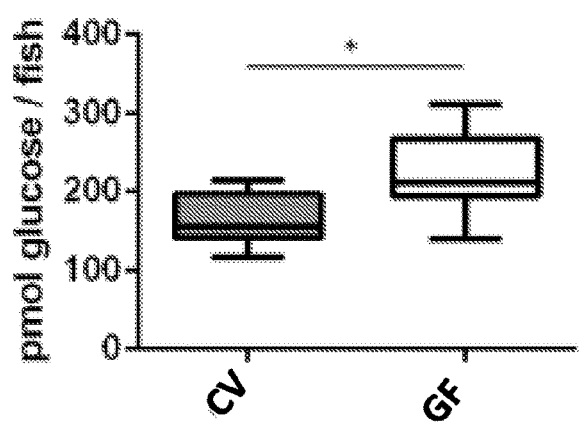

In order to determine whether this microbe-dependent β cell deficiency could affect the metabolic function of the fish, the levels of glucose present in both GF and CV larvae at 6 dpf were measured. The amount of glucose detected in GF fish was significantly higher than in CV fish (FIG. 1E), suggesting that GF fish are less efficient at importing and processing glucose from the blood, consistent with lower levels of circulating insulin in GF larvae with a paucity of β cells.

Figure 2A:
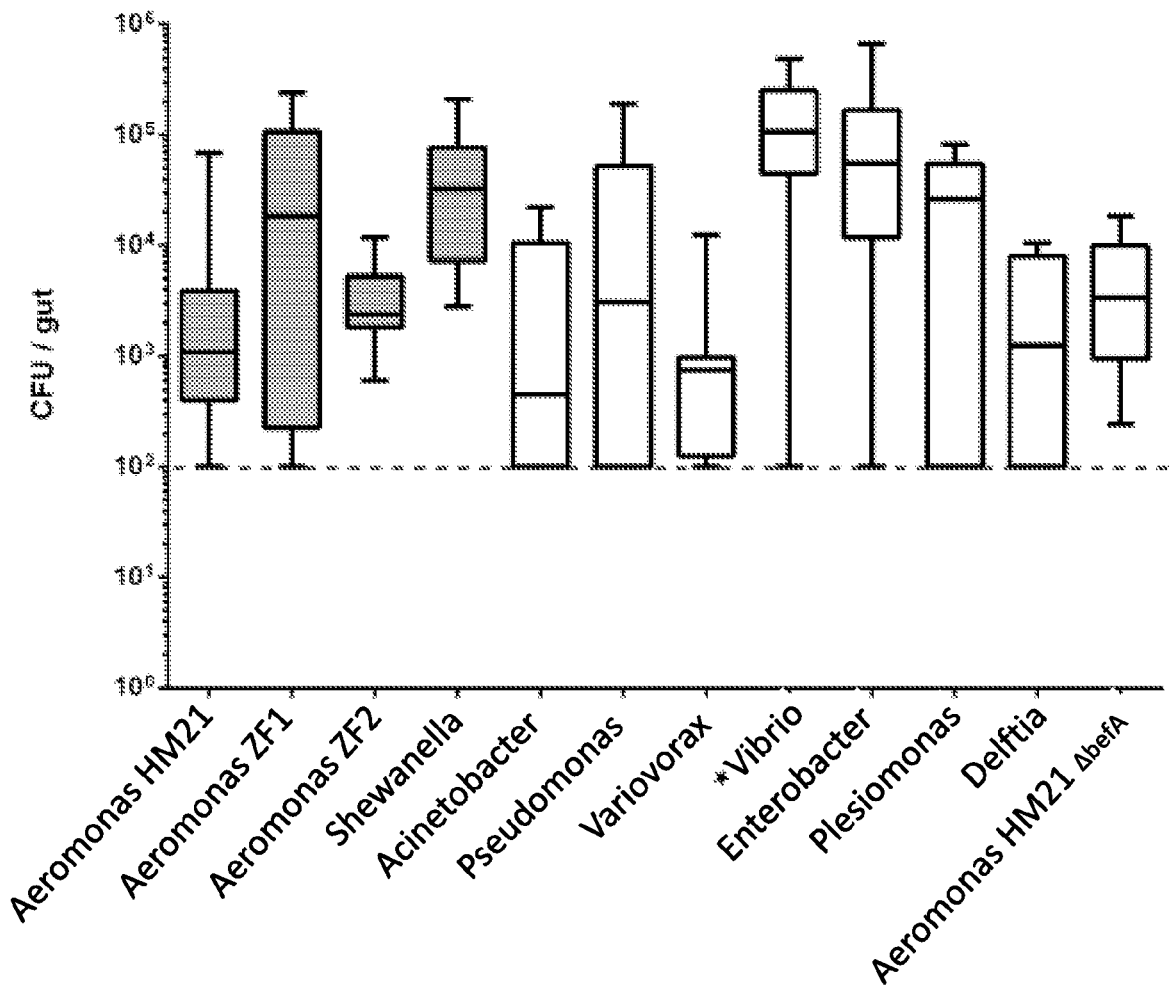
FIGS. 2A and 2B are graphs showing colony forming units (CFU) in zebrafish gut.
Figure 2B:
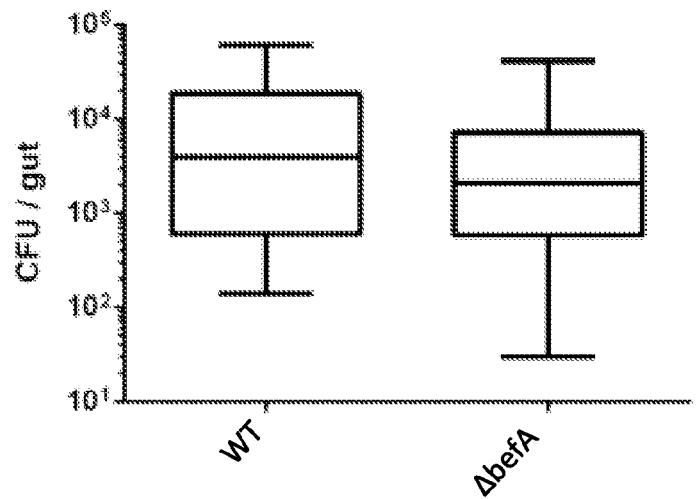

To investigate the possibility that a single bacterial species can promote β cell expansion, β cell numbers in larvae monoassociated at 4 dpf with bacterial isolates of the zebrafish intestinal microbiota that have been shown to colonize the larval gut in isolation were measured (FIG. 2). Three different species of the genus Aeromonas, and one species of the genus Shewanella were each sufficient to rescue GF β cell numbers to levels observed in CV fish (FIG. 1D), supporting the conclusion that specific members of the microbiota are capable of inducing expansion of the β cell mass.

Figure 3A:
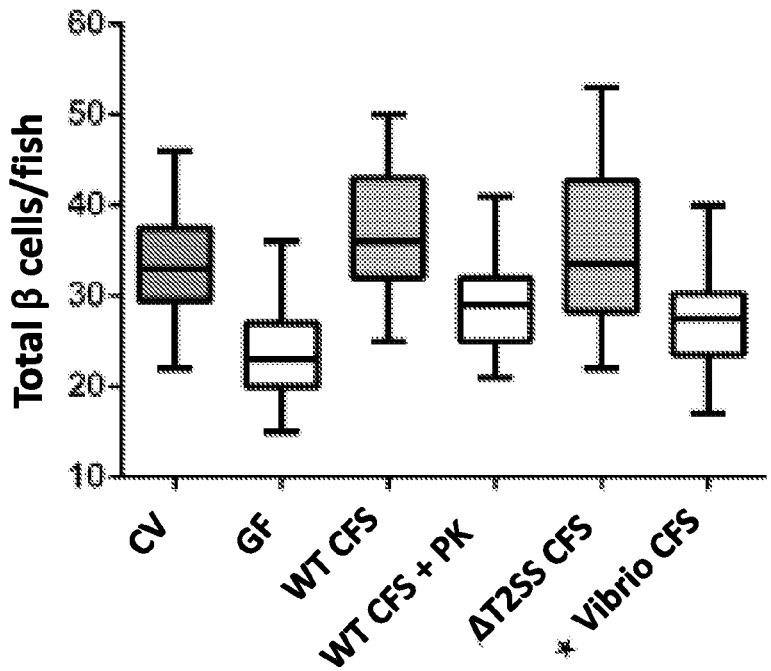
FIGS. 3A-3E are a series of panels showing the effect of a secreted protein on expansion of the β cell mass.

It is well documented that bacterial interactions with host organisms often involve secreted molecules or proteins. Therefore, to test whether a secreted bacterial factor(s) could influence β cell expansion, cell free supernatant (CFS) was harvested from overnight cultures of Aeromonas veronii HM21 (A. veronii), one of the species shown to rescue β cell expansion (FIG. 1D). The CFS from A. veronii cultures was added to GF larvae at 4 dpf. The CFS alone was able to restore GF β cell numbers (FIG. 3A), indicating that a secreted factor (or factors) was sufficient to induce normal β cell expansion. As a control, GF fish were treated with CFS from a Vibrio sp. isolate, which colonized the zebrafish gut (FIG. 2, ★), but did not induce β cell expansion (FIG. 1D, ★). This treatment was not significantly different from GF (FIG. 3A). Furthermore, the capacity to induce β cell numbers was lost when the A. veronii CFS sample was treated with proteinase K (FIG. 3A), indicating that the secreted factor(s) of interest was highly likely to be a protein.

In order to narrow down the list of candidates secreted by A. veronii, activity in the CFS of an A. veronii$^{\Delta T2SS}$ mutant strain lacking a functional type 2 secretion system (T2SS; Maltz et al., Appl. Environ Microbiol. 77:597-603, 2011), the major protein secretion pathway of Gram-negative bacteria (Cianciotto, Trends Microbiol. 13:581-588, 2005), was tested. Surprisingly, CFS harvested from the A. veronii$^{\Delta T2SS}$ strain was still sufficient to rescue GF β cell numbers (FIG. 3A). Ammonium sulfate precipitation was used to further separate proteins within the A. veronii$^{\Delta T2SS}$ CFS. One of these fractions was able to induce β cell numbers equivalent to those found in CV fish (FIG. 4A, 60-80% ammonium sulfate). Mass spectrometry was used to analyze the content of this fraction, which led to the identification of 187 distinct proteins (Table 1).

TABLE 1

Proteins in active fraction identified by mass spectrometry

| Spectral counts | Protein description |
|---|---|
| 188 | Peptide ABC transporter substrate-binding protein |
| 125 | Enolase |
| 91 | Elongation factor Ts |
| 87 | Uncharacterized protein |
| 74 | Dihydrolipoyl dehydrogenase |
| 71 | 50S ribosomal protein L9 |
| 70 | Phosphoenolpyruvate carboxykinase [ATP] |
| 69 | Glyceraldehyde-3-phosphate dehydrogenase |
| 62 | Membrane protein |
| 54 | Malate dehydrogenase |
| 54 | Azurin |
| 49 | Cytochrome C |
| 44 | Transaldolase |
| 41 | Triosephosphate isomerase |
| 40 | 50S ribosomal protein L1 |
| 40 | Fructose-bisphosphate aldolase |
| 37 | Putrescine-binding periplasmic protein |
| 37 | N utilization substance protein B homolog |
| 33 | Phosphoglycerate kinase |
| 29 | 50S ribosomal protein L19 |
| 29 | 50S ribosomal protein L7/L12 |
| 23 | C4-dicarboxylate ABC transporter substrate-binding protein |
| 22 | Sugar ABC transporter substrate-binding protein |
| 21 | LafB (Fragment) |
| 21 | Transporter |
| 20 | Uncharacterized protein |
| 20 | Universal stress protein |
| 19 | 10 kDa chaperonin |
| 19 | Superoxide dismutase |
| 18 | 2,3-bisphosphoglycerate-independent phosphoglycerate mutase |
| 18 | Uncharacterized protein |
| 16 | Transcriptional regulator |
| 15 | Chaperone protein DnaK |
| 15 | Probable thiol peroxidase |
| 15 | 50S ribosomal protein L10 |
| 14 | 30S ribosomal protein S30 |
| 14 | Thioredoxin |
| 14 | Uncharacterized protein |
| 13 | Serine protease |
| 13 | 30S ribosomal protein S16 |
| 13 | RNA polymerase-binding transcription factor DksA |
| 13 | Amino acid ABC transporter substrate-binding protein |
| 12 | 50S ribosomal protein L24 |
| 12 | Translation initiation factor IF-2 |
| 11 | 50S ribosomal protein L6 |
| 11 | Arginine ABC transporter substrate-binding protein |
| 11 | D-ribose transporter subunit RbsB |
| 11 | Elongation factor P |
| 11 | RNA-binding protein |
| 11 | Glutamine-tRNA ligase |
| 11 | Chemotaxis protein CheY |
| 10 | Peptidase M16 |
| 10 | 50S ribosomal protein L22 |
| 10 | UPF0234 protein |
| 10 | Succinyldiaminopimelate aminotransferase |
| 10 | Peptidyl-prolyl cis-trans isomerase |
| 10 | Transcriptional regulator |
| 9 | Fumarate hydratase |
| 9 | RNA chaperone/anti-terminator |

TABLE 1-continued

Proteins in active fraction identified by mass spectrometry

| Spectral counts | Protein description |
|---|---|
| 9 | Peptide ABC transporter substrate-binding protein |
| 9 | Methyl-galactoside ABC transporter substrate-binding protein |
| 9 | Methionine aminopeptidase |
| 9 | 30S ribosomal protein S6 |
| 9 | Ornithine carbamoyltransferase |
| 9 | Ribosome-recycling factor |
| 8 | Peptidyl-prolyl cis-trans isomerase |
| 8 | Uncharacterized protein |
| 8 | Uncharacterized protein |
| 8 | 30S ribosomal protein S1 |
| 7 | Anti-sigma D factor |
| 7 | Dihydrolipoamide succinyltransferase |
| 7 | Malonyl CoA-acyl carrier protein transacylase |
| 7 | Organic solvent ABC transporter substrate-binding protein |
| 6 | Phosphoribosylaminoimidazole-succinocarboxamide synthase |
| 6 | Acetate kinase |
| 6 | Uncharacterized protein |
| 6 | Cell wall assembly/cell proliferation coordinating protein |
| 6 | Elongation factor Tu (Fragment) |
| 6 | Iron ABC transporter substrate-binding protein |
| 6 | Deoxyribose-phosphate aldolase |
| 6 | Transcription elongation factor GreA |
| 6 | 50S ribosomal protein L25 |
| 6 | Tungsten ABC transporter substrate-binding protein |
| 6 | Cyclic diguanosine monophosphate-binding protein |
| 6 | Chaperone protein HtpG |
| 6 | RNA chaperone/anti-terminator |
| 6 | ABC transporter substrate-binding protein |
| 6 | Peptidase M54 |
| 5 | Thiosulfate sulfurtransferase |
| 5 | Isocitrate lyase |
| 5 | Lon protease |
| 5 | 3-hydroxydecanoyl-[acyl-carrier-protein] dehydratase |
| 5 | Glutamate--cysteine ligase |
| 5 | Amino acid ABC transporter substrate-binding protein |
| 5 | Phosphopentomutase |
| 5 | Peptidyl-prolyl cis-trans isomerase |
| 5 | Transcriptional regulator |
| 4 | DNA-directed RNA polymerase subunit alpha |
| 4 | Glutamate--tRNA ligase |
| 4 | Uncharacterized protein |
| 4 | 30S ribosomal protein S2 |
| 4 | Signal recognition particle receptor FtsY |
| 4 | 2',3'-cyclic nucleotide 2'-phosphodiesterase |
| 4 | Regulator of ribonuclease activity A |
| 4 | 30S ribosomal protein S17 |
| 4 | Exonuclease III |
| 4 | Uncharacterized protein |
| 4 | Acetylornithine aminotransferase |
| 4 | Endoribonuclease L-PSP |
| 4 | Cold-shock protein |
| 4 | Trigger factor |
| 4 | Glutamine--fructose-6-phosphate aminotransferase [isomerizing] |
| 4 | Methionine--tRNA ligase |
| 4 | Lysine--tRNA ligase |
| 4 | Uncharacterized protein |
| 4 | PTS glucose transporter subunit IIA |
| 4 | L-asparaginase |
| 4 | Anti-RNA polymerase sigma 70 factor |
| 4 | Elongation factor G |
| 3 | Uncharacterized protein |
| 3 | Phosphate-binding protein |
| 3 | Single-stranded DNA-binding protein |
| 3 | UDP-N-acetylglucosamine 1-carboxyvinyltransferase |
| 3 | Glutaredoxin |
| 3 | Preprotein translocase subunit Tim44 |
| 3 | 30S ribosomal protein S13 |
| 3 | 6,7-dimethyl-8-ribityllumazine synthase |
| 3 | Oxidoreductase |
| 3 | 50S ribosomal protein L11 |
| 3 | DNA-directed RNA polymerase subunit beta' |
| 3 | Translation initiation factor IF-I |
| 3 | Amino acid ABC transporter substrate-binding protein |
| 3 | Polyribonucleotide nucleotidyltransferase |
| 3 | Heme ABC transporter ATP-binding protein |
| 2 | Exodeoxyribonuclease V subunit gamma |
| 2 | Thiol:disulfide interchange protein |
| 2 | Uncharacterized protein |
| 2 | Peptidyl-tRNA hydrolase |
| 2 | Putative agmatine deiminase |
| 2 | Peptidoglycan-binding protein |
| 2 | Membrane protein |
| 2 | Outer membrane protein assembly factor BamC |
| 2 | Probable endonuclease 4 |
| 2 | Uncharacterized protein |
| 2 | Glucosaminidase |
| 2 | ABC transporter substrate-binding protein |
| 2 | 1-(5-phosphoribosyl)-5-[(5-phosphoribosylamino)methylideneamino] imidazole-4-carboxamide isomerase |
| 2 | PTS fructose transporter subunit IIC |
| 2 | Amidase |
| 2 | Molybdate ABC transporter substrate-binding protein |
| 2 | Membrane protein |
| 2 | Zn-dependent protease |
| 2 | Uncharacterized protein |
| 2 | Uncharacterized protein |
| 2 | Phosphoserine aminotransferase |
| 2 | Riboflavin synthase subunit alpha |
| 2 | Putrescine-binding periplasmic protein |
| 2 | Aldo/keto reductase |
| 2 | Uncharacterized protein |
| 2 | Chemotaxis protein CheW |
| 2 | Lipoprotein |
| 2 | Uncharacterized protein |
| 2 | Membrane protein |

To identify promising candidates from this list, the fact that zebrafish-associated bacterial isolates have differential abilities to induce larval β cells (FIG. 1D) was utilized. Basic local alignment search tool (BLAST) was used to identify those candidate proteins encoded by the genomes of bacterial strains that were sufficient to restore host β cells, and absent from those strains which were not sufficient. This approach identified a single gene, denoted by the locus tag, M0001_10165, predicted to encode a putative protein of 261 amino acids (protein highlighted in Table 1). The relative abundance of this candidate was low compared to other species detected within the CFS fraction, suggesting that it is a rare product of the bacterial microbiota.

Figure 3B:
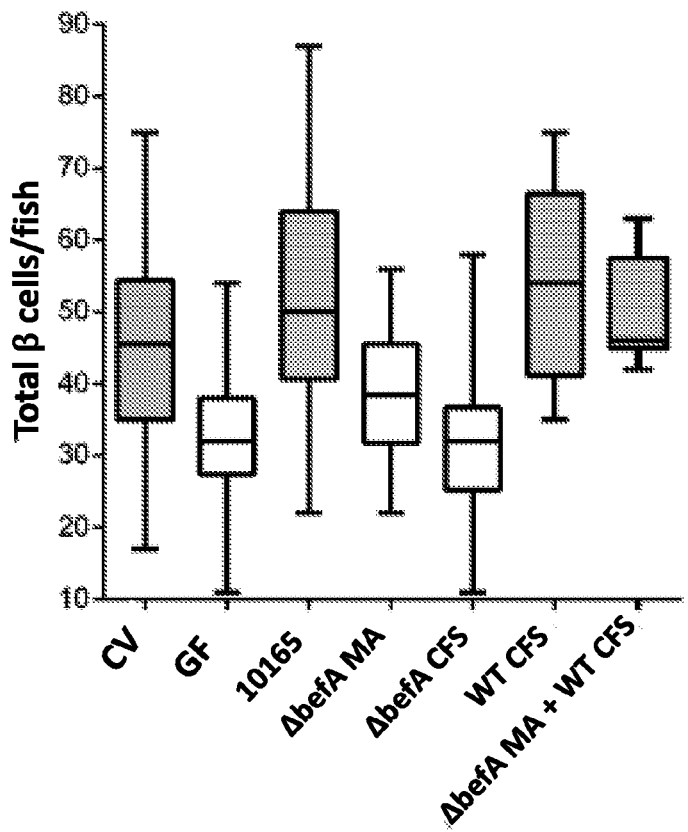
Figures 3C, 3D, 3E:
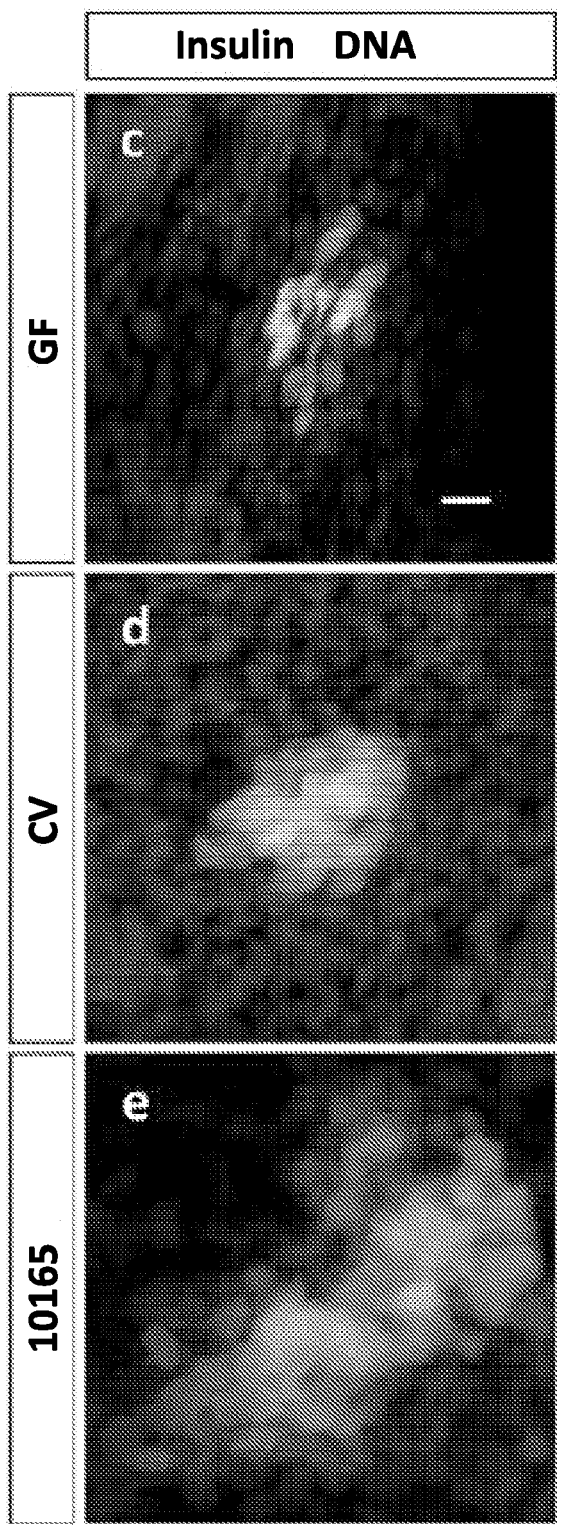

In order to test whether M001_10165 encoded the protein responsible for inducing β cell numbers, it was cloned it into an expression vector with an added C-terminal His tag for subsequent purification from BL21 Escherichia coli (FIG. 4B). Addition of purified M001_10165 (10165) protein to GF zebrafish larvae was sufficient to rescue β cell numbers (FIG. 3B). Image comparisons of the islets from differentially treated fish were striking, as both the CV and GF β cell populations were dwarfed by the expanded islets of several of the fish treated with 10165 (FIGS. 3C-E). Therefore, this protein has been named β cell Expansion Factor A (BefA), after its observed function in the zebrafish.

To determine whether the befA locus was necessary to induce an increase in β cell numbers in fish mono-associated with A. veronii, an A. veronii$^{\Delta befA}$ mutant strain was generated by replacing the coding region of befA with a chloramphenicol resistance gene. To ensure that the loss of the befA gene would not affect the ability of A. veronii to form a mono-association with the larvae, colonization assays were performed no deficiency in the ability of A. veronii$^{\Delta befA}$ to colonize the gut compared to A. veronii$^{WT}$ was observed (FIG. 2). GF fish were mono-associated with the *A. veronii*$^{\Delta befA}$ strain, or treated with its CFS from 4 to 6 dpf. Neither treatment was sufficient to rescue β cell numbers to CV totals (FIG. 3B). However, mono-associations of *A. veronii*$^{\Delta befA}$ could be complemented in trans with CFS from *A. veronii*$^{WT}$, which resulted in complete restoration of the β cell population (FIG. 3B). Taken together, these data demonstrate that a single protein, produced by a specific subset of bacteria within the zebrafish microbiota, is both necessary and sufficient for early β cell mass expansion.

Figures 5A, 5B, 5C, 5D, 5E, 5F:
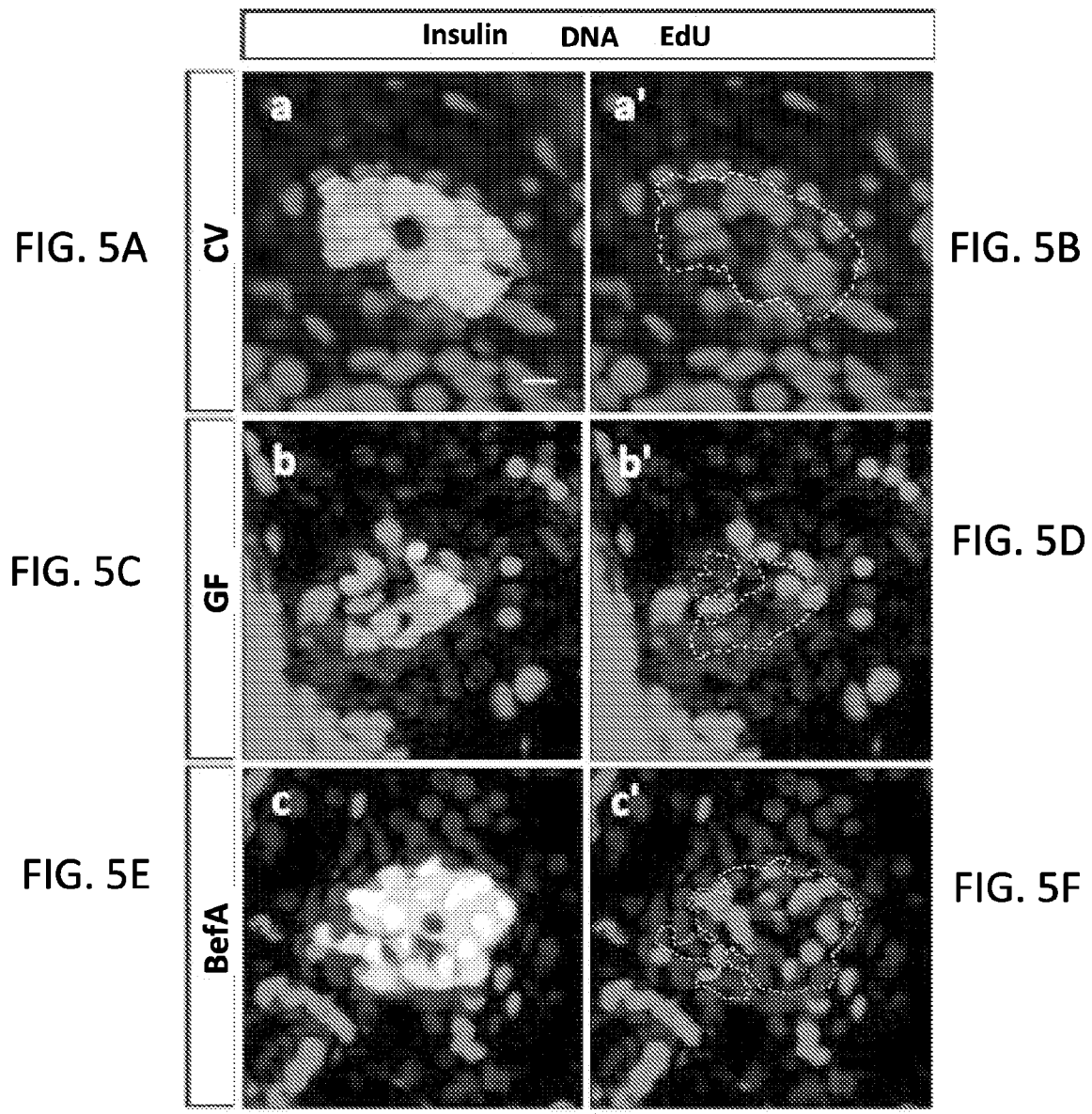
FIGS. 5A-5I are a series of panels showing the effect of BefA on β cell proliferation.
Figure 5G:
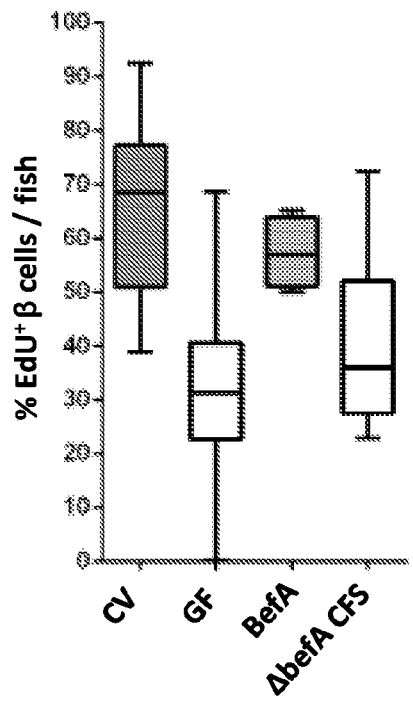

To understand how BefA induces zebrafish β cell expansion, whether BefA could increase β cell proliferation was tested. GF larvae were treated with BefA from 4 to 6 dpf in the presence of the thymidine analog, 5-ethynyl-2'-deoxyuridine (EdU). β cells of both BefA treated and CV fish exhibited significantly elevated levels of proliferation compared to GF fish (FIG. 5A-G). However, CFS from the *A. veronii*$^{\Delta befA}$ strain was not sufficient to increase proliferation rates in GF fish (FIG. 5G). These results suggest that BefA is both necessary and sufficient to increase basal rates of β cell proliferation during early larval development. This is the first demonstration that a bacterial-based product can cause β cell proliferation. Other mechanisms, such as neogenesis (Wang et al., *Development* 138:609-617, 2011) and trans-differentiation from alpha cells (Ye et al., *Development* 142:1407-1417, 2015), have been shown to contribute to the β cell population, and may also be influenced by BefA.

Figure 5H:
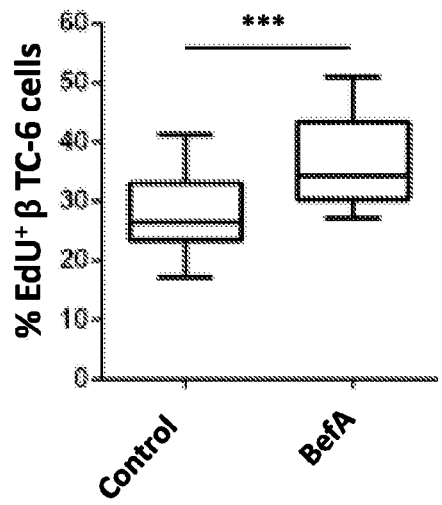
Figure 5I:
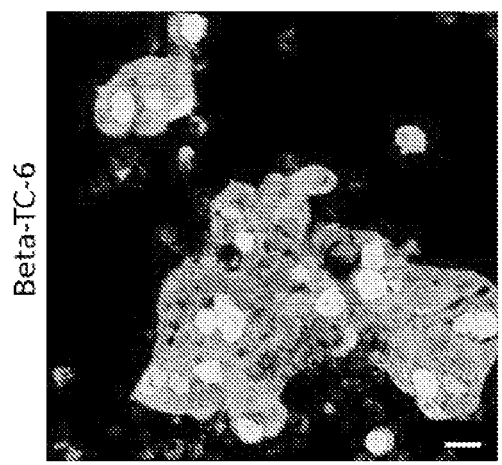

BefA was also tested for its effect on proliferation rates of mammalian β cells. BefA was added to murine 13-TC-6 cells (Poitout et al., *Diabetes* 44:306-313, 1995) in the presence of EdU (FIG. 5I). In samples treated with BefA, a significantly greater percentage of insulin expressing cells underwent cell division than in samples that did not receive the BefA treatment (FIG. 5H), showing that BefA, a bacterial product isolated from the zebrafish microbiota, is sufficient to increase proliferation in mammalian β cells.

Figure 6A:
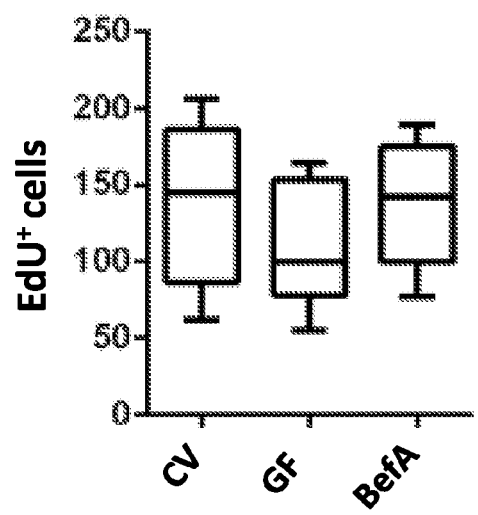
FIGS. 6A-6C are a series of panels showing β cell proliferation in zebrafish and mammalian cells.
Figure 6B:
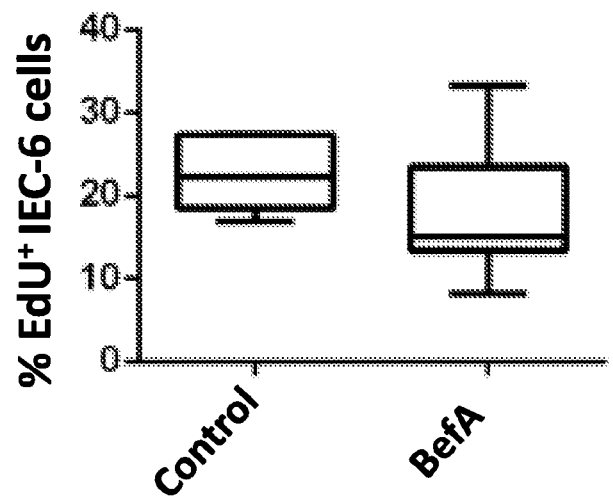
Figure 6C:
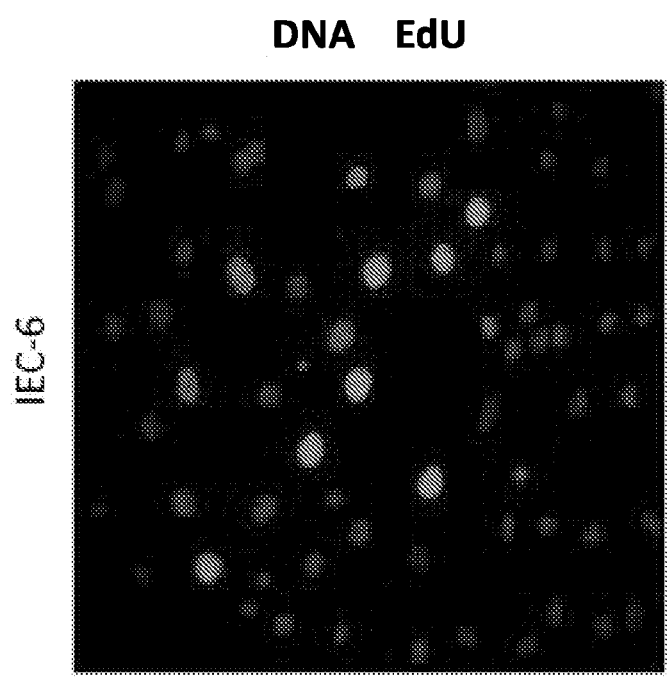

To gain insight into the specificity of BefA in host tissues, its ability to induce proliferation in both the exocrine pancreas and in the intestinal epithelium of zebrafish larvae was also tested. The levels of proliferation in these tissues were not changed across GF, CV and BefA treated larvae (FIGS. 6A and B), suggesting that BefA acts in a tissue-specific manner. Furthermore, BefA had no effect on levels of proliferation in the murine intestinal epithelial cell line IEC-6 (FIG. 6C), suggesting that BefA acts upon pancreatic endocrine tissue from multiple species.

Although befA is not required for the formation of mono-associations, it could be important to bacterial fitness by playing a role as a colonization factor. Colonization factor genes are often important for competition within the host environment. Therefore to investigate a potential role for befA in bacterial competition, GF fish were co-inoculated with equal concentrations of *A. veronii*$^{WT}$ and *A. veronii*$^{\Delta befA}$. Interestingly, after allowing 48 hours for colonization to occur, the *A. veronii*$^{\Delta befA}$ strain was outcompeted in the gut by *A. veronii*$^{WT}$ (FIG. 2B), suggesting that befA could play an important fitness role for *A. veronii* as a colonization factor gene.

Figure 7A:
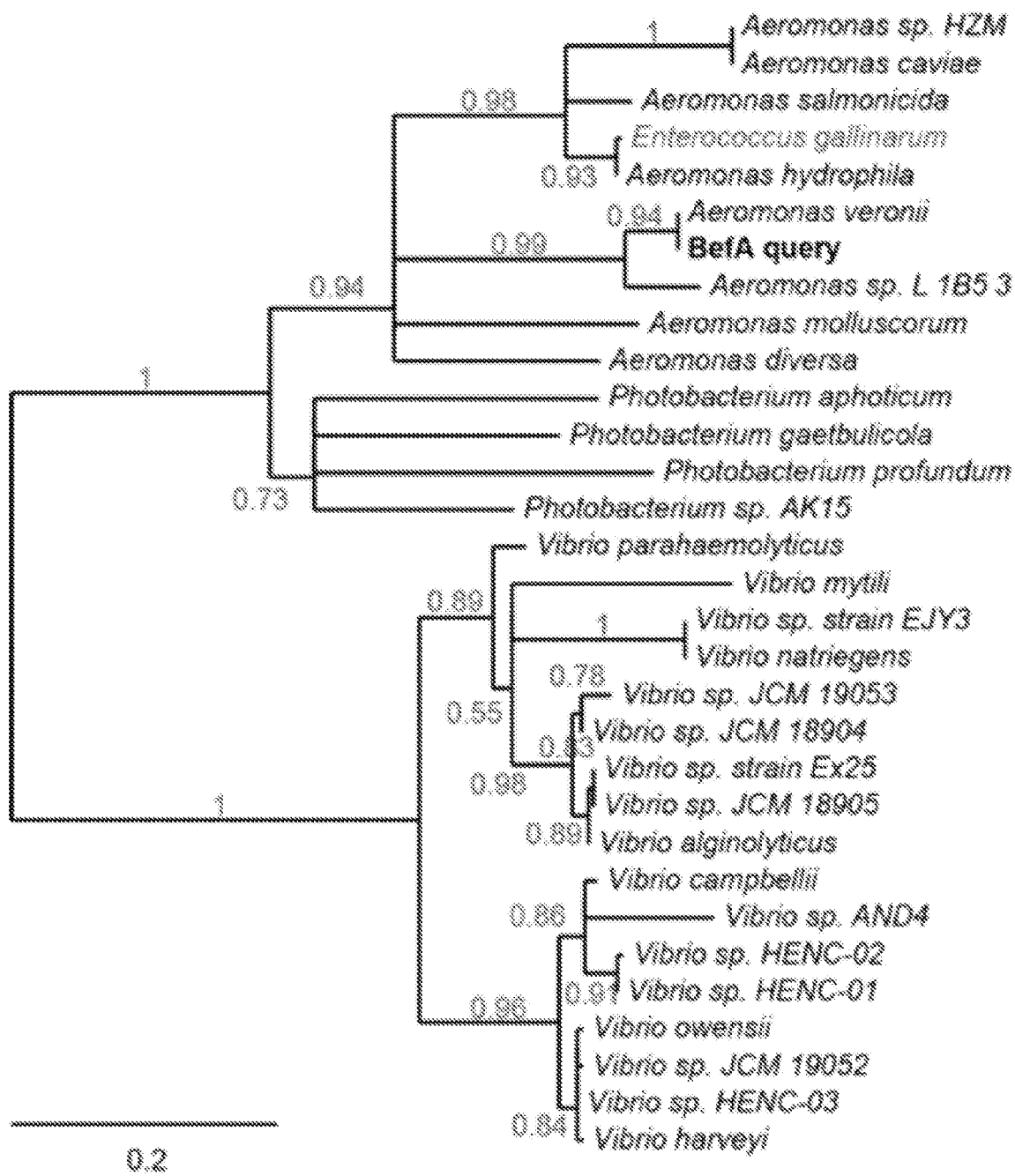
FIGS. 7A and 7B are phylogenetic trees of homologs of BefA across microbial species.
Figure 7B:
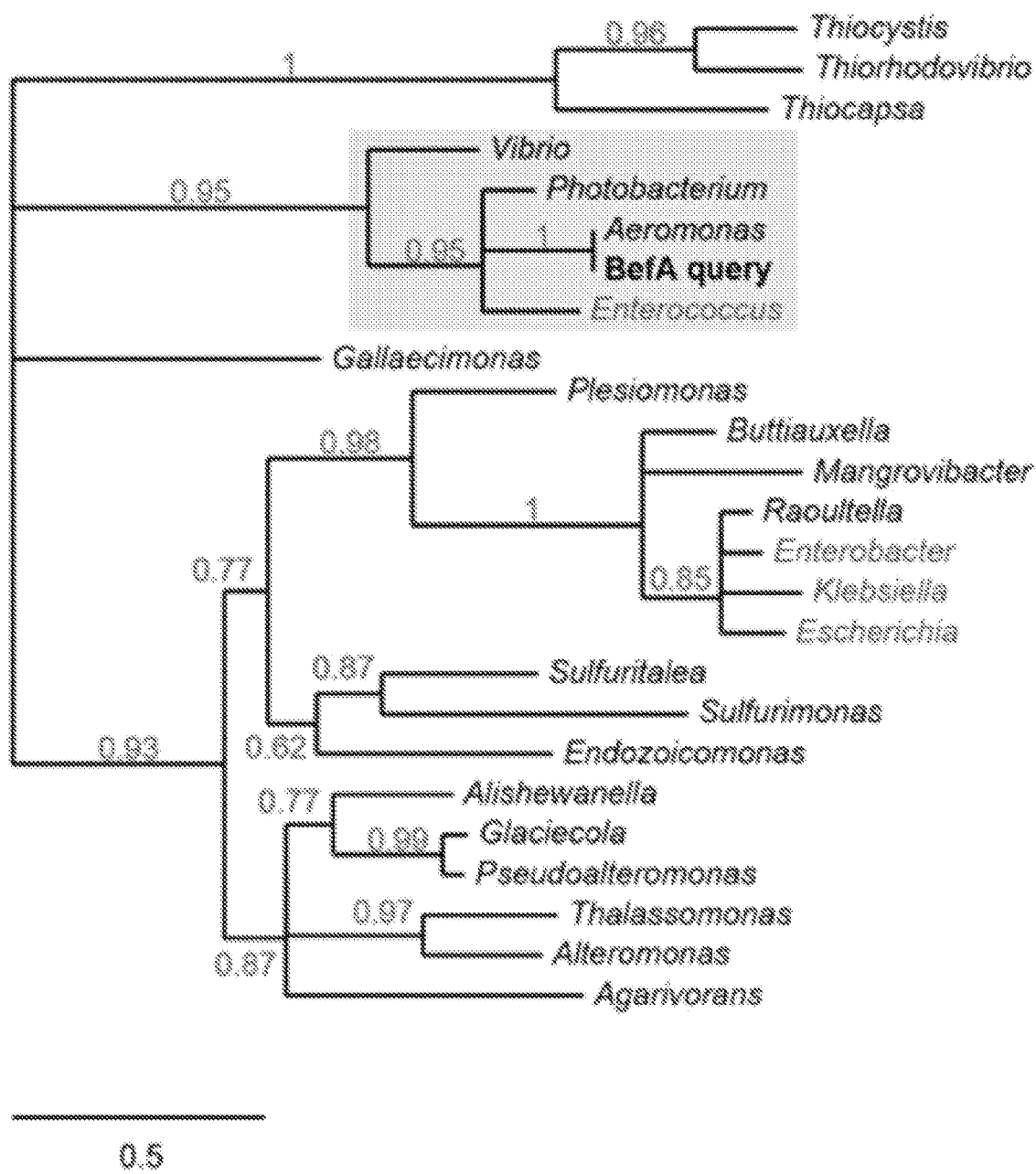

Phylogenetic analysis of BefA revealed a close homolog (82% amino acid sequence identity) in the human-associated species *Enterococcus gallinarum*, along with homologs in many species of the *Aeromonas*, *Vibrio*, and *Photobacterium* genera (FIG. 7A). Widening the search to include more distant homologs identified potentially related genes in three additional human-associated genera: *Enterobacter*, *Escherichia*, and *Klebsiella* (FIG. 7B). These results suggest that a similar host-microbe signaling mechanism could exist within humans. Additionally, the BefA amino acid sequence contains a putative SYLF domain in the C-terminal, and this domain is also predicted within each human-associated homolog of BefA. Interestingly, the domain is conserved across the kingdom of life and has lipid-binding function in more complex organisms (Hasegawa et al., *J. Cell Biol.* 193:901-906, 2011).

Example 3

Methods of Screening for Modulators of β Cell Number

This example describes particular methods that can be used for screening for modulators of β cell number utilizing transgenic zebrafish that express GFP under the control of the insulin promoter. One skilled in the art will appreciate that methods that deviate from these specific methods can also be used to successfully screen for modulators of β cell number.

Day 1: Set up Ins: GFP fish to cross naturally. Use dividers to prevent egg laying until the morning.

Day 2 (0 dpf):
1. By 9:00 am, move natural crosses into tanks with fresh water and pull dividers to allow fish to mate. Prepare antibiotic EM to collect eggs (100 µg/mL ampicillin, 5 µg/mL kanamycin, and 250 µg/ml amphotericin B, sterile filtered). Collect eggs in antibiotic EM and place in 30° C. incubator until they reach shield stage.
2. Move embryos into sterile 50-mL beaker. Wash embryos 3× in sterile EM. Immerse embryos in 0.1% PVP-I solution for 2 minutes. Rinse 3× in sterile EM. Transfer embryos to a new sterile 50-mL beaker and immerse in 0.003% bleach for 20 minutes. Pour off bleach and rinse 3× in sterile EM. Transfer 20-25 embryos into sterile cell culture flasks with 50-mL sterile EM.

Day 5 (3 dpf):
1. Start overnight bacterial cultures. Start 50-mL cultures of bacteria for testing CFS for beta cell proliferation activity.

Day 6 (4 dpf):
1. Follow CFS preparation protocol listed above (Example 2).
2. Visually check GF fish flasks for bacteria.
3. Inoculate flasks with $10^6$ cfu/ml bacteria of interest or with 500 ng/ml concentrated CFS of interest. For each experiment, include one CV flask as a control and a GF flask as a control. Collect 1-mL of flask water before inoculation to plate and confirm that flasks were germ free at the start of the experiment.

Day 8 (6 dpf):
1. Check the plates with the inoculation water to ensure the flasks were germ-free before the experiment started.
2. One flask at a time, add tricaine to the fish to anesthetize them. Use a glass pipette to carefully pull each fish out of the flask and place it into a 1.5 mL tube. Put up to 20 fish of the same treatment into a single tube. Remove all excess EM from the tube and add 1 mL of 4% PFA in PBS with 0.1% Triton X. Place tubes at 4° C. with gentle rocking overnight.

Day 9: Processing for imaging
1. If detecting EdU, follow protocol above according to the manufacturer's protocol. Each tube of fish can be treated as one "cover slip" in the protocol.
2. Add TO-PRO® nuclear stain as described above in 2% BSA and leave at 4° C. overnight with gentle rocking.

3. Wash each tube 8 times for at least 15 minutes at room temperature with 1 mL of PBS. Mount whole fish onto a glass slide. Orient the fish so that they are lying with the right side of the body facing up to most easily visualize the pancreatic islet.
4. Use confocal microscopy to scan the entire islet using a 60× objective with a Z-stack size of roughly 20 μM, and a step size of 0.2 μM to ensure good resolution of all the beta cells in the islet.

Quantify beta cells by counting the total number of nuclei that express GFP.

Example 4

Method of Determining Effect of BefA Proteins on β Cells in a Mammalian Subject This example describes particular methods that can be used to determine the effect of BefA or related proteins on β cell number or proliferation in a mammalian subject. One skilled in the art will appreciate that methods that deviate from these specific methods can also be successfully used.

In order to determine whether BefA (such as SEQ ID NOs: 1-7 disclosed herein) or a related protein can increase the β cell mass in mice, a transgenic mouse model with the insulin promoter driving expression of a fluorescent marker (such as GFP) or a mouse model of diabetes (such as the NOD mouse model) is utilized. Purified BefA protein or a bacterial strain common to the mouse intestinal microbiota, such as E. coli, engineered to overproduce and secrete BefA is administered (for example, via oral gavage into the gastrointestinal tract) according to standard protocols. Adult and newborn mice can be tested. After several days (e.g., 1-7 days), mice are sacrificed and the β cell mass is quantified according to histology techniques and compared to mice treated with appropriate controls. β cell proliferation is analyzed by processing histological sections with EdU. In diabetes model mice, the incidence and/or severity of disease symptoms is also monitored. An increase in β cell mass and/or β cell proliferation compared to control mice indicates that the protein increases β cell number. A decrease in the incidence of diabetes and/or in the number or severity of symptoms in diabetes model mice also indicates that the protein increases β cell number and/or can be used to treat or inhibit diabetes.

Example 5

Method of Treating or Inhibiting Diabetes

This example describes particular methods that can be used to treat or inhibit diabetes and/or increase β cell number or proliferation in a subject. However, one skilled in the art will appreciate that methods that deviate from these specific methods can also be successfully used.

Based upon the teaching disclosed herein, β cell number can be increased and diabetes can be treated or inhibited by administering an effective amount of a composition including an Aeromonas protein increasing β cell number, a nucleic acid encoding the protein, or a preparation including cells that produce the protein or a cell-free supernatant from such cells to a subject with diabetes.

In an example, a subject with diabetes (such as a subject with Type I diabetes) is identified and selected for treatment. Following subject selection, an effective dose of the composition or preparation including the protein increasing β cell number, nucleic acid, or cells or cell-free supernatant described above is administered to the subject. The amount of the composition or preparation administered to prevent, reduce, inhibit, and/or treat diabetes depends on the subject being treated, the severity of the disorder, and the manner of administration of the composition. Ideally, an effective amount of an agent is the amount sufficient to prevent, reduce, and/or inhibit, and/or treat the condition (e.g., diabetes) in a subject without causing substantial adverse effects in the subject.

In one specific example, a protein increasing β cell number (such as a protein comprising, consisting essentially of, or consisting of the sequence of SEQ ID NOs: 1-7), a fragment thereof (such as a SYLF domain, for example, amino acids 114-258 of any one of SEQ ID NOs: 1-3), or a cell expressing the protein or fragment thereof, is administered to a subject. For example, a protein increasing β cell number is administered to a subject at about 1 mg to 1 g daily. In another example, a protein increasing β cell number is administered at about 1 mg to 1 g biweekly or weekly. In further examples, a nucleic acid encoding a protein increasing β cell number (such as SEQ ID NOs: 8-11) is administered to a subject at about 1 mg to 1 g daily, biweekly, or weekly. An appropriate dose can be selected by a skilled clinician based on the subject, the condition being treated and other factors.

Subjects are monitored by methods known to those skilled in the art to determine responsiveness of the subject to the treatment. For example, the symptoms of the subject are monitored, for example blood glucose levels, blood insulin levels, insulin sensitivity index, homeostatic model assessment score, quantitative insulin sensitivity check index score (QUICKI; Katz et al., *J. Clin. Endocrinol. Metab.* 85:2402-2410, 2000), or a combination of two or more thereof. It is contemplated that additional agents can be administered, such as additional diabetes therapeutics in combination with or following treatment with the Aeromonas protein increasing β cell number.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method for treating or inhibiting diabetes in a subject, comprising administering to the subject an effective amount of:
   a polypeptide comprising an amino acid sequence having at least 95% sequence identity to the amino acid sequence of any one of SEQ ID NOs: 1-7,
   thereby treating or inhibiting diabetes in the subject.

2. The method of claim 1, wherein treating or inhibiting diabetes comprises increasing β cell number and/or proliferation in the subject.

3. The method of claim 1, wherein the effective amount of the polypeptide administered to the subject is about 1 mg to about 5 g.

4. The method of claim 1, wherein the effective amount of the polypeptide is administered to the subject daily, weekly, or monthly.

5. The method of claim 1, further comprising administering one or more additional diabetes therapies to the subject.

6. A method for increasing β cell number or proliferation, comprising contacting pancreatic cells with an effective amount of:
   a polypeptide comprising an amino acid sequence having at least 95% sequence identity to the amino acid sequence of any one of SEQ ID NOs: 1-7,
   thereby increasing β cell number or proliferation.

7. The method of claim 6, wherein contacting pancreatic cells comprises administering the polypeptide to a subject.

8. The method of claim 7, wherein the subject has diabetes.

9. The method of claim 7, wherein the subject is a fish.

10. The method of claim 8, further comprising administering one or more additional diabetes therapies to the subject.

11. The method of claim 1, wherein the polypeptide comprises the amino acid sequence of any one of SEQ ID NOs: 1-7.

12. The method of claim 11, wherein the polypeptide consists of the amino acid sequence of any one of SEQ ID NOs: 1-7.

13. The method of claim 11, wherein the polypeptide is encoded by a nucleic acid comprising the sequence of any one of SEQ ID NOs: 8-11.

14. The method of claim 6, wherein the polypeptide comprises the amino acid sequence of any one of SEQ ID NOs: 1-7.

15. The method of claim 14, wherein the polypeptide consists of the amino acid sequence of any one of SEQ ID NOs: 1-7.

16. The method of claim 14, wherein the polypeptide is encoded by a nucleic acid comprising the sequence of any one of SEQ ID NOs: 8-11.

* * * * *

SEQUENCE LISTING

```
<160> NUMBER OF SEQ ID NOS: 13

<210> SEQ ID NO 1
<211> LENGTH: 261
<212> TYPE: PRT
<213> ORGANISM: Aeromonas veronii

<400> SEQUENCE: 1
```

```
Met Asn Lys Arg Asn Trp Leu Leu Ala Leu Ser Leu Ser Leu Ala Phe
1               5                   10                  15

Ser Pro Cys Tyr Ala Asp Trp Ala Lys Leu Lys Ala Ala Ser Asp
            20                  25                  30

Leu Gly Ala Ala Val Ser Glu Thr Ser Lys Glu Val Trp Gln Asp Val
        35                  40                  45

Ser Asp Phe Ser Lys Lys Ser Trp Ala Ser Ile Ser Ala Trp Gly Glu
50                  55                  60

Glu Ala Phe Asn Thr Ala Gly Val Trp Thr Asp Lys Ser Ile Ala Thr
65                  70                  75                  80

Gly Lys Glu Trp Leu Lys Ala Ala Asp Lys Glu Leu Asn Glu Met Leu
                85                  90                  95

Asn Pro Lys Thr Ala Lys Glu Ala Arg Ile Ala Ile Asn Thr Met Ala
            100                 105                 110

Asp Thr Ala Leu Ile Arg Leu Phe Asn Glu Gln Pro Ser Ala Lys Leu
        115                 120                 125

Leu Phe Asp Lys Ala Tyr Gly Tyr Ala Val Phe Asp Ser Arg Lys Phe
130                 135                 140

Ser Leu Met Leu His Thr Asn Gln Gly Ala Gly Val Ala Val Asn Arg
145                 150                 155                 160

Lys Thr Gly Lys His Thr Tyr Met Lys Met Phe Gly Ala Gly Leu Ala
                165                 170                 175

Ala Gly Ile Gly Gly Lys Phe Tyr Gln Gln Val Ile Leu Phe Glu Asp
            180                 185                 190

Lys Ala Arg Phe Asp Ala Phe Val Thr Gln Gly Trp Glu Ala Thr Ser
        195                 200                 205

Glu Val Gly Val Val Ala Gly Lys Glu Ser Ala Glu Leu Thr Ala Lys
210                 215                 220

Tyr Asn Gly Gly Met Ala Ile Tyr Gln Ile Gly Glu Lys Gly Leu Leu
225                 230                 235                 240

Leu Asp Ala Asn Ile Ser Gly Ser Lys Tyr Trp Ile Asp Lys Asp Leu
                245                 250                 255

Thr Glu Thr Ser Arg
            260

<210> SEQ ID NO 2
<211> LENGTH: 258
<212> TYPE: PRT
<213> ORGANISM: Aeromonas sp. ZOR0001

<400> SEQUENCE: 2

Met Asn Lys Arg Asn Trp Leu Leu Ala Leu Ser Leu Ser Leu Ala Phe
1               5                   10                  15

Ser Pro Cys Tyr Ala Asp Trp Ala Lys Leu Lys Ala Ala Ser Asp
            20                  25                  30

Leu Gly Ala Ala Val Ser Glu Thr Ser Lys Glu Val Trp Gln Asp Val
        35                  40                  45

Ser Asp Phe Ser Lys Lys Ser Trp Ala Ser Ile Ser Ala Trp Gly Glu
50                  55                  60

Asp Ala Phe Asn Thr Ala Gly Val Trp Thr Asp Lys Ser Ile Ala Thr
65                  70                  75                  80

Gly Lys Glu Trp Leu Lys Ala Ala Asp Lys Glu Leu Asn Glu Met Leu
                85                  90                  95

Asn Pro Lys Thr Ala Lys Glu Ala Arg Ile Ala Leu Asn Thr Met Ala
```

```
                    100                 105                 110
Asp Thr Ala Leu Ile Arg Leu Phe Asn Glu Gln Pro Ser Ala Lys Leu
            115                 120                 125

Leu Phe Asp Lys Ala Tyr Gly Tyr Ala Val Phe Asp Ser Arg Lys Phe
        130                 135                 140

Ser Leu Met Leu His Thr Asn Gln Gly Ala Gly Val Ala Val Asn Arg
145                 150                 155                 160

Lys Thr Gly Lys His Thr Tyr Met Lys Met Phe Gly Ala Gly Leu Ala
                165                 170                 175

Ala Gly Ile Gly Gly Lys Phe Tyr Gln Gln Val Val Leu Phe Glu Asp
            180                 185                 190

Lys Ala Arg Phe Asp Ala Phe Val Thr Gln Gly Trp Glu Ala Thr Ser
        195                 200                 205

Glu Val Gly Val Val Ala Gly Lys Glu Ser Ala Glu Leu Thr Ala Lys
    210                 215                 220

Tyr Asn Gly Gly Met Ala Ile Tyr Gln Ile Gly Glu Lys Gly Leu Leu
225                 230                 235                 240

Leu Asp Ala Asn Ile Ser Gly Ser Lys Tyr Trp Ile Asp Lys Asp Leu
                245                 250                 255

Thr Gln

<210> SEQ ID NO 3
<211> LENGTH: 258
<212> TYPE: PRT
<213> ORGANISM: Aeromonas sp. ZOR0002

<400> SEQUENCE: 3

Met Lys Ile Arg Phe Leu Val Ile Ala Thr Ala Leu Ala Leu Ala Ser
1               5                   10                  15

Thr Pro Gly Leu Ala Asp Trp Ala Lys Leu Lys Glu Ala Ala Ser Glu
            20                  25                  30

Leu Gly Thr Ala Val Ser Asp Thr Ser Lys Glu Ala Trp Lys Gly Ile
        35                  40                  45

Thr Asp Phe Ser Lys Glu Thr Trp Glu Ser Val Ser Ser Trp Gly Ala
    50                  55                  60

Glu Ala Tyr Asn Lys Ala Gly Ala Trp Thr Ala Glu Ser Ala Ala Thr
65                  70                  75                  80

Gly Lys Glu Trp Leu Thr Ala Ala Asp Lys Lys Leu Asp Thr Met Leu
                85                  90                  95

Glu Pro Lys Thr Pro Glu Glu Ala Arg Thr Ala Leu Asp Thr Met Ala
            100                 105                 110

Asp Thr Ala Leu Val Arg Leu Phe Asn Glu Gln Pro Ser Ala Lys Leu
        115                 120                 125

Leu Phe Asp Lys Ala Tyr Gly Tyr Ala Val Phe Asp Ser Arg Lys Phe
    130                 135                 140

Ser Leu Met Ile His Thr Asn Gln Gly Ala Gly Val Ala Val Asn Arg
145                 150                 155                 160

Thr Ser Gly Lys His Thr Tyr Met Lys Met Phe Gly Ala Gly Leu Ala
                165                 170                 175

Ala Gly Ile Gly Gly Lys Phe Tyr Gln Gln Val Ile Leu Phe Glu Asp
            180                 185                 190

Lys Ala Arg Phe Asp Ala Phe Val Ser Lys Gly Trp Glu Ala Thr Ser
        195                 200                 205

Glu Val Gly Ala Val Ala Gly Lys Glu Ser Ala Glu Leu Thr Ala Lys
```

```
                210               215               220
Tyr Asn Gly Gly Met Ala Ile Tyr Gln Ile Gly Glu Lys Gly Leu Leu
225                 230               235               240

Leu Asp Ala Asn Ile Ser Gly Ser Lys Tyr Trp Leu Asp Asp Leu
                245               250               255

Asn Lys

<210> SEQ ID NO 4
<211> LENGTH: 193
<212> TYPE: PRT
<213> ORGANISM: Shewanella sp. ZOR0012

<400> SEQUENCE: 4

Met Lys Ser Ile Leu Ser Phe Val Val Ala Ser Thr Cys Leu Ile Ala
1               5                   10                  15

Ser Leu Leu Thr Pro Val Ala Gln Ala Asp Asp Ser Tyr Thr Glu Ala
                20                  25                  30

Leu Lys Asn Phe His Gln Ala Lys Glu Thr Arg Lys Phe Phe Asp Thr
            35                  40                  45

Ala Tyr Gly Tyr Ala Leu Phe Pro Thr Val Gly Lys Gly Ile Gly
        50                  55                  60

Ile Gly Ala Ala Tyr Gly Lys Gly Arg Val Phe Gln Ala Gly Gln Tyr
65                  70                  75                  80

Met Gly Asp Ser Ser Leu Thr Gln Leu Ser Ile Gly Phe Gln Leu Gly
                85                  90                  95

Gly Gln Ala Tyr Ser Glu Ile Ile Phe Phe Lys Asp Ala Lys Ser Tyr
            100                 105                 110

Asn Glu Phe Thr Ser Gly Ser Phe Glu Phe Asp Ala Gln Ala Ser Ala
        115                 120                 125

Val Ala Ile Asn Met Gly Ala Asn Ala Lys Ala Gly Thr Thr Gly Asn
    130                 135                 140

Ser Ala Gly Ala Gly Gln Ala Gly Gly Asn Gln Ser Ala Thr Ala Ala
145                 150                 155                 160

Tyr Ile Asn Gly Met Ala Val Phe Thr Val Ala Lys Gly Gly Leu Met
                165                 170                 175

Phe Glu Ala Ala Leu Ala Gly Gln Ser Phe Thr Phe Glu Pro Arg Gly
            180                 185                 190

Asn

<210> SEQ ID NO 5
<211> LENGTH: 195
<212> TYPE: PRT
<213> ORGANISM: Klebsiella pneumoniae

<400> SEQUENCE: 5

Met Lys Leu Gln Thr Leu Phe Leu Val Ala Met Thr Ala Leu Ala Gly
1               5                   10                  15

Cys Ser Ala Gln Gly Asp Thr Ala Ser Gln Arg Ala Ser Ile Gln
                20                  25                  30

Lys Met Arg Asn Glu Thr Leu Thr Lys Leu Tyr Thr Leu Gln Pro Glu
            35                  40                  45

Ala Arg Ser Asp Ile Gln His Ala Lys Gly Tyr Ala Val Phe Ala Asn
        50                  55                  60

Asn Ser Ser Lys Ile Leu Leu Phe Gly Phe Gly Ser Gly Tyr Gly Val
65                  70                  75                  80
```

```
Val Arg Asp Thr Ala Ser Gly Lys Asp Thr Tyr Met Lys Met Ala Gln
                85                  90                  95

Gly Gly Ala Gly Leu Gly Ile Gly Ile Lys Gln Gln Arg Thr Val Leu
            100                 105                 110

Val Phe His Asp Lys Ala Ala Leu Asp Arg Phe Ile Arg Gln Gly Tyr
            115                 120                 125

Met Val Gly Ala Asp Ala Asn Ala Ala Lys Tyr Asp Asp Lys Gly
            130                 135                 140

Ile Ala Pro Ile Ala Ala Ser Ala Asn Gly Val Ala Lys Asp Thr Ser
145                 150                 155                 160

Ser Leu Pro Ser Lys Val Asn Val Tyr Glu Ile Thr Asp Lys Gly Leu
                165                 170                 175

Ala Ala Gln Ala Met Val Asn Gly Tyr Lys Tyr Trp Pro Asp Asp Glu
            180                 185                 190

Leu Asn Pro
        195

<210> SEQ ID NO 6
<211> LENGTH: 258
<212> TYPE: PRT
<213> ORGANISM: Enterococcus gallinarum

<400> SEQUENCE: 6

Met Lys Ile Arg Phe Leu Val Ile Ala Thr Ala Leu Ala Leu Thr Ser
1               5                   10                  15

Ala Pro Gly Leu Ala Asp Trp Ala Lys Val Lys Ala Ala Thr Glu
            20                  25                  30

Leu Gly Asn Ala Val Ser Asp Thr Ser Lys Glu Ala Trp Gln Ser Val
            35                  40                  45

Thr Asp Phe Ser Lys Ala Thr Trp Ala Ser Val Ser Gln Trp Gly Ser
    50                  55                  60

Glu Ala Phe Asn Thr Ala Gly Ala Trp Thr Asp Lys Ser Val Ala Thr
65                  70                  75                  80

Gly Lys Glu Trp Leu Ala Val Ala Asp Lys Lys Leu Asp Glu Met Leu
                85                  90                  95

Glu Pro Lys Thr Ala Asp Glu Ala Arg Leu Ala Leu Asn Thr Met Ala
            100                 105                 110

Asp Thr Ala Leu Val Arg Leu Phe Asn Glu Gln Pro Ser Ala Lys Leu
            115                 120                 125

Leu Phe Asp Lys Ala Tyr Gly Tyr Ala Val Phe Asp Ser Arg Lys Phe
            130                 135                 140

Ser Leu Met Leu His Thr Asn Gln Gly Ala Gly Val Ala Val Asn Arg
145                 150                 155                 160

Ala Thr Gly Lys His Thr Tyr Met Lys Met Phe Gly Ala Gly Leu Ala
                165                 170                 175

Ala Gly Leu Gly Gly Lys Phe Tyr Gln Gln Val Ile Leu Phe Glu Asp
            180                 185                 190

Lys Ala Arg Phe Asp Ala Phe Val Ser Gln Gly Trp Glu Ala Thr Ser
            195                 200                 205

Glu Val Gly Ala Val Ala Gly Lys Glu Ser Ala Glu Leu Thr Ala Lys
        210                 215                 220

Tyr Asn Gly Gly Met Ala Ile Tyr Gln Ile Gly Glu Lys Gly Leu Leu
225                 230                 235                 240

Leu Asp Ala Asn Ile Ser Gly Ser Lys Tyr Trp Val Asp Lys Asp Leu
                245                 250                 255
```

<210> SEQ ID NO 7
<211> LENGTH: 256
<212> TYPE: PRT
<213> ORGANISM: Photobacterium sp.

<400> SEQUENCE: 7

Met Lys Leu Lys Leu Ile Val Val Ala Leu Cys Leu Ala Val Ala Pro
1               5                   10                  15

Ala His Ala Ser Trp Glu Glu Ile Lys Lys Ala Ala Ser Asp Leu Gly
            20                  25                  30

Gln Lys Val Ser Glu Gly Ser Lys Lys Ala Trp Glu Asp Val Thr Asp
        35                  40                  45

Phe Ser Lys Glu Thr Trp Asp Ser Val Ser Glu Trp Gly Glu Asp Ala
    50                  55                  60

Phe Asn Thr Ala Gly Glu Trp Thr Asp Ala Ser Ile Glu Lys Gly Lys
65                  70                  75                  80

Glu Trp Leu Glu Ala Gly Glu Ala Lys Leu Asn Glu Met Leu Glu Pro
                85                  90                  95

Glu Thr Pro Glu Glu Ala Arg Leu Ala Leu Asp Thr Met Ser Asp Thr
            100                 105                 110

Ala Leu Val Arg Leu Phe Asn Glu Pro Ser Ala Lys Leu Leu Phe
        115                 120                 125

Asp Thr Ala Tyr Gly Tyr Ala Val Phe Asp Ser Arg Lys Phe Ser Leu
    130                 135                 140

Met Leu His Thr Asn Gln Gly Ala Gly Val Ala Val Asp Arg Lys Thr
145                 150                 155                 160

Gly Lys Arg Thr Tyr Met Lys Met Phe Gly Ala Gly Leu Ala Leu Gly
                165                 170                 175

Leu Gly Gly Lys Phe Tyr Gln Gln Leu Ile Phe Phe Glu Asp Lys Lys
            180                 185                 190

Thr Phe Asp Ser Phe Val Lys Asp Gly Trp Glu Ala Thr Ser Glu Ala
        195                 200                 205

Gly Ala Val Ala Gly Thr Glu Ser Ala Glu Leu Thr Ala Lys Tyr Asn
    210                 215                 220

Gly Gly Met Ala Ile Tyr Gln Ile Gly Glu Lys Gly Leu Leu Leu Asp
225                 230                 235                 240

Ala Asn Ile Ser Gly Ser Lys Tyr Trp Val Asp Glu Asp Leu Thr Gln
                245                 250                 255

<210> SEQ ID NO 8
<211> LENGTH: 786
<212> TYPE: DNA
<213> ORGANISM: Aeromonas veronii

<400> SEQUENCE: 8
atgaacaagc gtaactggtt gctggccttg tcactgagtc tggccttctc accctgttat      60
gccgactggg ccaagctcaa ggccgcagcg tccgatctgg gagcggcagt gagcgagacc     120
agcaaggagg tgtggcagga tgtcagcgat ttctccaaga gagctgggc ttccatctct      180 gcatggggtg aagaggcgtt caataccgcc ggggtctgga ccgacaagag catcgcgacc     240
ggcaaggagt ggctgaaggc agccgacaag gagctcaacg agatgctcaa ccccaagacg     300
gcgaaagagg cgaggatcgc gatcaatacc atggccgaca ctgcgctgat ccggttgttc     360

| | |
|---|---|
| aacgagcagc catcagccaa gttgttgttt gacaaggctt atggttatgc ggtgttcgat | 420 |
| tcgcgcaagt tctccctgat gctgcatacc aatcaggggg ccggggtggc agtcaatcgc | 480 |
| aaaaccggca agcacaccta tatgaagatg tttggtgcgg gtctggcggc cgggattggc | 540 |
| ggcaagttct atcagcaggt gatcctgttt gaagacaagg ccagattcga tgccttcgtg | 600 |
| acccaggggt gggaagctac ctccgaagtg ggtgtggtgg ccggcaagga gagcgctgag | 660 |
| ctgaccgcca aatataatgg cggcatggcc atctaccaga ttggcgagaa gggtttgctg | 720 |
| ctcgatgcca atatctccgg ctctaaatac tggattgaca aggacttgac tgaaacgagc | 780 |
| cgctaa | 786 |

<210> SEQ ID NO 9
<211> LENGTH: 777
<212> TYPE: DNA
<213> ORGANISM: Aeromonas sp. ZOR0001

<400> SEQUENCE: 9

| | |
|---|---|
| atgaacaagc gtaactggtt gctggccttg tcactgagtc tggccttctc accctgttat | 60 |
| gccgactggg ccaagctcaa ggccgcagcg tccgatctgg gagcggcagt gagcgagacc | 120 |
| agcaaggagg tgtggcagga tgtcagcgat ttttccaaaa agagctgggc ctccatctcg | 180 |
| gcttggggag aggatgcctt caataccgcc ggggtctgga ccgacaagag catcgcgaca | 240 |
| ggcaaggagt ggctgaaggc agccgacaag gagctcaacg agatgctcaa ccccaagacg | 300 |
| gcgaaagagg cgaggatcgc gctcaatacc atggccgaca ctgcgctgat ccggttgttc | 360 |
| aacgagcagc catcagccaa gttgttgttt gacaaggctt atggctatgc agtgttcgat | 420 |
| tcgcgcaagt tctccctgat gctgcatacc aatcaggggg ccggggtggc agtcaatcgc | 480 |
| aaaaccggca agcacaccta tatgaagatg tttggcgcag gtctggcggc cgggattggc | 540 |
| ggcaagttct atcagcaggt ggtcctgttt gaagacaagg ccagattcga tgccttcgtg | 600 |
| acccaggggt gggaggccac ctccgaagtg ggcgtggtgg ccggcaagga gagcgccgag | 660 |
| cttaccgcca aatacaatgg cggcatggcc atctaccaga ttggtgagaa gggcctgctg | 720 |
| ctcgatgcca atatctccgg ctccaagtac tggattgaca aggacttgac tcaataa | 777 |

<210> SEQ ID NO 10
<211> LENGTH: 777
<212> TYPE: DNA
<213> ORGANISM: Aeromonas ZOR0002

<400> SEQUENCE: 10

| | |
|---|---|
| atgaagattc gattcctggt gatagccacg gcactggcgc tggcctcgac ccccggtctg | 60 |
| gccgactggg caaagctgaa ggaggccgcc tccgaactcg gtaccgcggt gagcgatacc | 120 |
| agcaaggagg cgtggaaggg gatcaccgat ttttccaagg agacctggga gtcggtgtcc | 180 |
| agctgggggg ccgaggccta caacaaggcg ggggcctgga cggcagagag cgcggccacc | 240 |
| ggcaaggagt ggctgaccgc cgccgacaag aagctcgaca ccatgctcga gcccaagacc | 300 |
| ccggaggagg cgagaaccgc cctcgatacc atggccgata ccgccctggt gcggctattc | 360 |
| aacgagcagc cctcggccaa gttgctgttt gacaaggctt atggctatgc ggtgttcgac | 420 |
| tcgcgcaagt tctccctgat gatccacacc aatcaggggg ccggggtggc cgtcaatcgc | 480 |
| accagtggca agcacaccta catgaagatg ttcggtgccg gtctcgcggc cgggatcggc | 540 |
| ggcaagttct accagcaggt gatcctgttc gaagacaagg cgaggttcga tgccttcgtc | 600 |
| agcaaggggt gggaagccac ctccgaggtg gcgccgtgg cggcaagga gagcgccgag | 660 |

```
ctcaccgcca aatacaatgg cggcatggcc atctaccaga ttggcgagaa ggggctgttg      720
cttgacgcca acatctcggg ctccaagtac tggctggatg atgacctgaa caagtga        777

<210> SEQ ID NO 11
<211> LENGTH: 582
<212> TYPE: DNA
<213> ORGANISM: Shewanella sp. ZOR0012

<400> SEQUENCE: 11
atgaaatcaa ttttatcttt tgttgtcgca tcgacctgct tgattgccag cttactgaca      60
ccagttgcgc aagcagatga tagttacact gaggctttaa aaaattttca ccaagccaag     120
gaaacccgca aatttttga taccgcctat ggctacgccc tctttccaac agttggcaaa      180
ggtgggattg gtattggcgc cgcctacggc aaaggtcggg tttttcaagc gggacaatat     240
atgggagact ccagcctaac ccagctatct attggatttc aattaggtgg acaagcctat     300
agtgaaatca tcttctttaa agatgccaaa tcctacaatg agttcaccag tggcagtttt     360
gagtttgatg cccaagcctc cgcagttgcc attaatatgg gtgctaacgc caaagcaggc     420
accacaggca actcggcagg tgctggtcaa gccggtggta atcaatcggc taccgcagcc     480
tatatcaatg gtatggcggt ctttaccgtt gccaagggtg gactaatgtt tgaagccgca     540
ctggcgggac aatcttttac cttcgagcct aggggtaact aa                       582

<210> SEQ ID NO 12
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 12
gcccatatga tgaacaagcg taactggttg ctg                                  33

<210> SEQ ID NO 13
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 13
ggcctcgagg cggctcgttt cagtcaagtc                                      30
```